United States Patent
Kallmyer

(10) Patent No.: US 9,295,850 B2
(45) Date of Patent: Mar. 29, 2016

(54) CHARGE-BALANCING DURING ELECTRICAL STIMULATION

(71) Applicant: Medtronic, Inc., Minneapolis, MN (US)

(72) Inventor: Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 25 days.

(21) Appl. No.: 13/827,595

(22) Filed: Mar. 14, 2013

(65) Prior Publication Data

US 2013/0282079 A1 Oct. 24, 2013

Related U.S. Application Data

(60) Provisional application No. 61/637,643, filed on Apr. 24, 2012.

(51) Int. Cl.
*A61N 1/372* (2006.01)
*A61N 1/36* (2006.01)

(52) U.S. Cl.
CPC .............. *A61N 1/37252* (2013.01); *A61N 1/36* (2013.01); *A61N 1/3605* (2013.01); *A61N 1/3606* (2013.01); *A61N 1/3615* (2013.01); *A61N 1/36125* (2013.01); *A61N 1/36128* (2013.01); *A61N 1/36082* (2013.01); *A61N 1/36142* (2013.01)

(58) Field of Classification Search
CPC ....... A61N 1/08; A61N 1/36146; A61N 1/36; A61N 1/3605; A61N 1/3606; A61N 1/36125; A61N 1/37252
USPC .................................................. 607/62, 2, 66
See application file for complete search history.

(56) References Cited

U.S. PATENT DOCUMENTS 2,534,043 A * 12/1950 MacPhail ................. A61N 1/38
                                                                    307/110
3,211,154 A * 10/1965 Becker et al. ..................... 607/5
(Continued)

FOREIGN PATENT DOCUMENTS

WO        9623546 A1    8/1996
WO    2006121424 A2    11/2006

OTHER PUBLICATIONS

Liu, Xiao et al., "Generation of Balanced Biphasic Stimulus Current with Integrated Blocking Capacitor," Proceedings of the 2005 European Conference on Circuit Theory and Design., vol. 3, Aug. 28-Sep. 2, 2005, pp. III/19-III/22 (4 pages).
(Continued)

*Primary Examiner* — Christopher A Flory
(74) *Attorney, Agent, or Firm* — Shumaker & Sieffert, P.A.

(57) ABSTRACT

In some examples, a device for delivering electrical stimulation to a medical patient includes an electrical stimulation generator, a coupling circuit, and a processing module. The electrical stimulation generator is configured to generate electrical stimulation. The coupling circuit includes a first node connected to the electrical stimulation generator, a second node configured to deliver the electrical stimulation to the patient, and a capacitor. The coupling circuit is configured to operate in a first state to couple the capacitor between the first and second nodes in a first orientation and operate in a second state to couple the capacitor between the first and second nodes in a second orientation that is opposite to the first orientation. The processing module is configured to set the state of the coupling circuit to one of the first and second states.

25 Claims, 19 Drawing Sheets

(56) References Cited

U.S. PATENT DOCUMENTS

| | | | | |
|---|---|---|---|---|
| 3,342,176 A * | 9/1967 | Kaplan et al. | | 600/519 |
| 3,389,704 A * | 6/1968 | Buchowski et al. | | 607/2 |
| 3,391,697 A * | 7/1968 | Greatbatch | A61N 1/362 | 331/112 |
| 3,453,486 A * | 7/1969 | Weber | | 315/391 |
| 3,453,546 A * | 7/1969 | Fryer | | 340/870.17 |
| 3,478,746 A * | 11/1969 | Greatbatch | A61N 1/0587 | 607/9 |
| 3,495,584 A * | 2/1970 | Schwalm | | 600/508 |
| 3,563,247 A * | 2/1971 | Bowers | | 607/13 |
| 3,618,615 A * | 11/1971 | Greatbatch | A61N 1/3708 | 607/28 |
| 3,648,707 A * | 3/1972 | Greatbatch | A61N 1/368 | 607/9 |
| 3,707,974 A * | 1/1973 | Raddi | A61N 1/362 | 607/11 |
| 3,835,865 A * | 9/1974 | Bowers | A61N 1/365 | 607/13 |
| 3,893,462 A | 7/1975 | Manning | | |
| 4,331,145 A * | 5/1982 | Winter | | 604/20 |
| 4,343,312 A * | 8/1982 | Cals et al. | | 607/13 |
| 4,466,440 A * | 8/1984 | Money et al. | | 607/9 |
| 4,533,988 A * | 8/1985 | Daly | H02M 7/217 | 128/903 |
| 4,592,359 A | 6/1986 | Galbraith | | |
| 4,726,379 A | 2/1988 | Altman et al. | | |
| 4,792,777 A * | 12/1988 | Masaki | | 338/80 |
| 4,821,724 A * | 4/1989 | Whigham | A61N 1/365 | 607/13 |
| 4,903,700 A * | 2/1990 | Whigham et al. | | 607/13 |
| 4,991,583 A * | 2/1991 | Silvian | | 607/11 |
| 5,083,562 A * | 1/1992 | de Coriolis | A61N 1/3956 | 607/7 |
| 5,222,494 A | 6/1993 | Baker, Jr. | | |
| 5,300,096 A * | 4/1994 | Hall et al. | | 607/48 |
| 5,336,242 A * | 8/1994 | Zadeh | | 607/11 |
| 5,395,395 A * | 3/1995 | Hedberg | A61N 1/39 | 607/5 |
| 5,405,357 A * | 4/1995 | Rowe-Lanzisera et al. | | 606/204 |
| 5,413,591 A * | 5/1995 | Knoll | A61N 1/3956 | 607/6 |
| 5,431,692 A * | 7/1995 | Hansen et al. | | 607/28 |
| 5,433,737 A * | 7/1995 | Aimone | | 607/72 |
| 5,591,217 A * | 1/1997 | Barreras | | 607/61 |
| 5,601,610 A * | 2/1997 | Persson | | 607/5 |
| 5,713,931 A * | 2/1998 | Paul | A61N 1/3708 | 607/27 |
| 5,733,309 A * | 3/1998 | Kroll et al. | | 607/5 |
| 5,735,887 A * | 4/1998 | Barreras et al. | | 607/60 |
| 5,766,124 A * | 6/1998 | Polson | | 600/13 |
| 5,782,880 A * | 7/1998 | Lahtinen | A61N 1/362 | 607/72 |
| 5,782,884 A * | 7/1998 | Stotts | A61N 1/36521 | 607/17 |
| 5,824,016 A * | 10/1998 | Ekwall | | 607/9 |
| 5,836,981 A * | 11/1998 | Chang et al. | | 607/9 |
| 5,843,136 A | 12/1998 | Zhu et al. | | |
| 6,035,237 A | 3/2000 | Schulman et al. | | |
| 6,067,474 A * | 5/2000 | Schulman et al. | | 607/57 |
| 6,076,015 A * | 6/2000 | Hartley et al. | | 607/20 |
| 6,208,896 B1 * | 3/2001 | Mulhauser | | 607/5 |
| 6,209,764 B1 * | 4/2001 | Hartlaub et al. | | 223/94 |
| 6,212,429 B1 * | 4/2001 | Sullivan et al. | | 607/5 |
| 6,236,892 B1 * | 5/2001 | Feler | | 607/117 |
| 6,280,461 B1 * | 8/2001 | Glegyak et al. | | 607/5 |
| 6,463,326 B1 * | 10/2002 | Hartley et al. | | 607/20 |
| 6,473,649 B1 * | 10/2002 | Gryzwa et al. | | 607/28 |
| 6,539,255 B1 * | 3/2003 | Brewer et al. | | 607/5 |
| 6,647,290 B2 * | 11/2003 | Wuthrich | | 607/5 |
| 7,221,977 B1 * | 5/2007 | Weaver | A61N 1/3708 | 320/136 |
| 7,848,804 B1 | 12/2010 | Kroll et al. | | |
| 7,852,052 B2 * | 12/2010 | Vernon | | 323/269 |
| RE43,374 E * | 5/2012 | Kronberg | A61N 1/326 | 607/51 |
| 8,265,769 B2 * | 9/2012 | Denison | A61N 1/3702 | 330/9 |
| 2001/0051817 A1 * | 12/2001 | Sullivan et al. | | 607/5 |
| 2002/0040192 A1 * | 4/2002 | Prutchi | A61B 5/4869 | 600/536 |
| 2003/0074025 A1 * | 4/2003 | Wuthrich | | 607/5 |
| 2003/0120323 A1 * | 6/2003 | Meadows et al. | | 607/46 |
| 2005/0096701 A1 * | 5/2005 | Donovan et al. | | 607/2 |
| 2005/0245970 A1 * | 11/2005 | Erickson et al. | | 607/2 |
| 2006/0142688 A1 * | 6/2006 | Kon | A61N 1/0412 | 604/20 |
| 2007/0060968 A1 * | 3/2007 | Strother | A61N 1/36007 | 607/34 |
| 2007/0299483 A1 * | 12/2007 | Strother | A61N 1/37276 | 607/48 |
| 2008/0140171 A1 * | 6/2008 | Roberts et al. | | 607/142 |
| 2008/0183098 A1 * | 7/2008 | Denison | A61B 5/0002 | 600/547 |
| 2009/0062880 A1 * | 3/2009 | Li et al. | | 607/32 |
| 2009/0270943 A1 * | 10/2009 | Maschino | A61N 1/36114 | 607/45 |
| 2010/0063399 A1 * | 3/2010 | Walker et al. | | 600/459 |
| 2010/0327887 A1 * | 12/2010 | Denison | A61B 5/0002 | 324/692 |
| 2011/0009916 A1 | 1/2011 | Efimov et al. | | |
| 2011/0160803 A1 * | 6/2011 | Stessman et al. | | 607/62 |
| 2011/0190849 A1 * | 8/2011 | Faltys et al. | | 607/50 |
| 2012/0116483 A1 * | 5/2012 | Yonezawa et al. | | 607/74 |
| 2012/0185018 A1 * | 7/2012 | Cilingiroglu | | 607/65 |
| 2013/0035735 A1 * | 2/2013 | Kroll | | 607/4 |
| 2013/0282079 A1 * | 10/2013 | Kallmyer | | 607/62 |
| 2014/0088656 A1 * | 3/2014 | Cabelka et al. | | 607/2 |
| 2014/0214113 A1 * | 7/2014 | Greiner et al. | | 607/39 |

OTHER PUBLICATIONS

International Search Report and Written Opinion from International Application No. PCT/US2013/035791, dated Feb. 7, 2014, 10 pages.

* cited by examiner

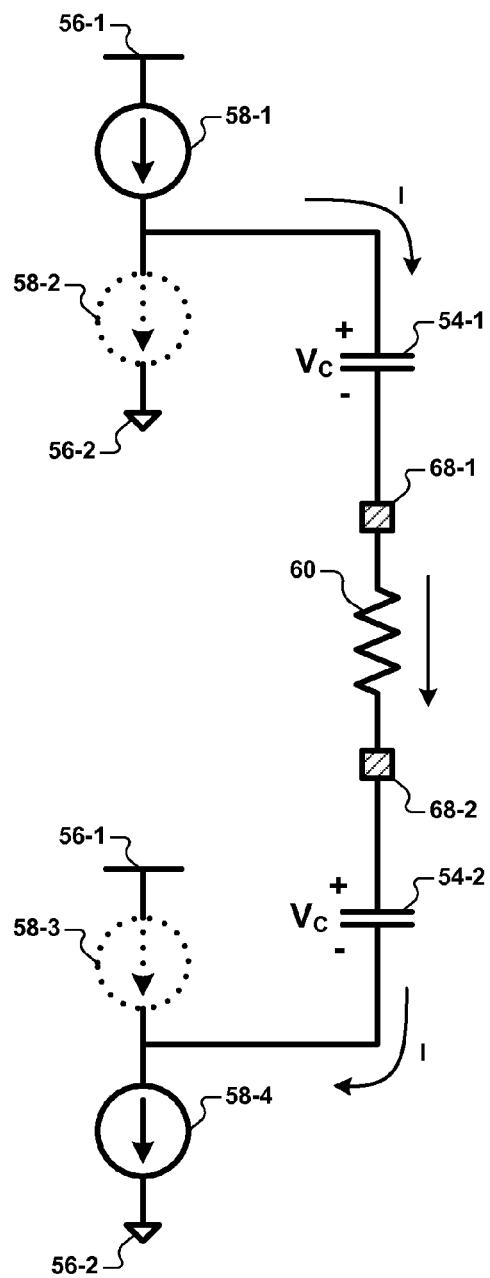
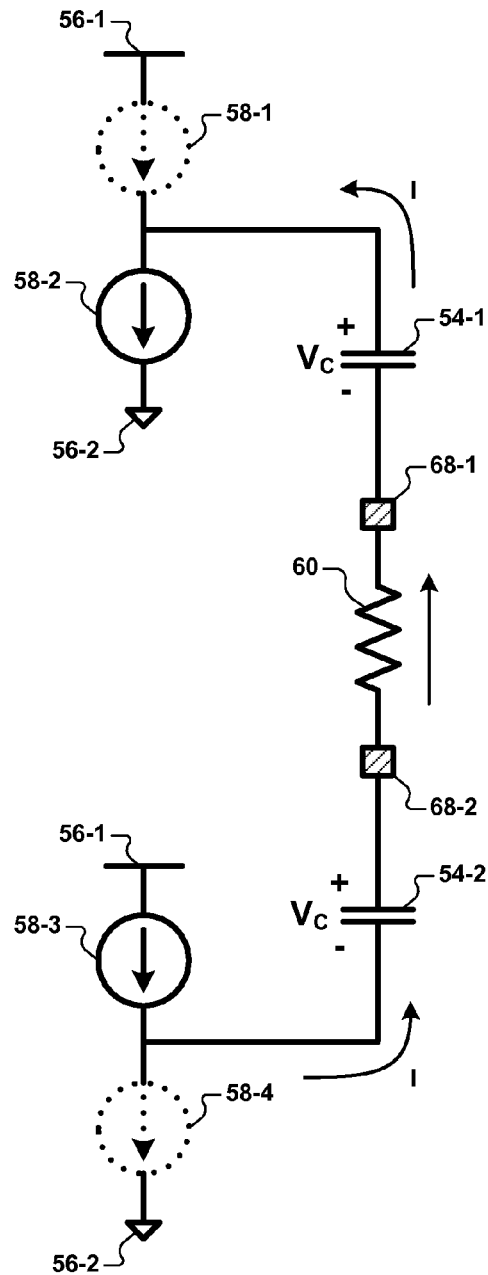
FIG. 4A　　　　　FIG. 4B

CHARGE-BALANCING DURING ELECTRICAL STIMULATION

This application claims the benefit of U.S. Provisional Application No. 61/637,643, filed Apr. 24, 2012, the entire content of which is incorporated herein by reference.

TECHNICAL FIELD

The disclosure relates to techniques for coupling electrical stimulation generators to stimulation electrodes.

BACKGROUND

Implantable or external electrical stimulators deliver electrical stimulation therapy to a target tissue site within a patient with the aid of one or more electrodes, which may be deployed by medical leads. Electrical stimulators may be used in different therapeutic applications, such as cardiac pacing, deep brain stimulation (DBS), spinal cord stimulation (SCS), pelvic stimulation, gastric stimulation, peripheral nerve stimulation, and functional electrical stimulation. Electrical stimulation may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, or psychiatric disorders.

SUMMARY

An electrical stimulation device of the present disclosure includes coupling circuits that capacitively couple a stimulation generator of the electrical stimulation device to stimulation electrodes of the stimulation device.

In some examples, a device for delivering electrical stimulation to a patient according to the present disclosure comprises circuitry configured to deliver an electrical stimulation current of a first polarity to the patient via a capacitor. The circuitry is further configured to switch a terminal of the capacitor into which the electrical stimulation current flows at least once during delivery of the electrical stimulation current of the first polarity.

In some examples, a device for delivering electrical stimulation to a patient according to the present disclosure comprises means for delivering an electrical stimulation current of a first polarity to the patient via a capacitor. The device further comprises means for switching a terminal of the capacitor into which the electrical stimulation current flows at least once during delivery of the electrical stimulation current of the first polarity.

In some examples, a method for delivering electrical stimulation to a patient according to the present disclosure comprises delivering an electrical stimulation current of a first polarity to the patient via a capacitor. The method further comprises switching a terminal of the capacitor into which the electrical stimulation current flows at least once during delivery of the electrical stimulation current of the first polarity.

In some examples, a device for delivering electrical stimulation to a patient according to the present disclosure comprises an electrical stimulation generator, a coupling circuit, and a processing module. The electrical stimulation generator is configured to generate electrical stimulation. The coupling circuit comprises a first node connected to the electrical stimulation generator, a second node configured to deliver the electrical stimulation to the patient, and a capacitor. The coupling circuit is configured to operate in a first state to couple the capacitor between the first and second nodes in a first orientation and operate in a second state to couple the capacitor between the first and second nodes in a second orientation that is opposite to the first orientation. The processing module is configured to set the state of the coupling circuit to one of the first and second states.

In some examples, a device for delivering electrical stimulation to a patient according to the present disclosure comprises an electrical stimulation generator, a coupling circuit, and a processing module. The electrical stimulation generator is configured to generate a biphasic electrical stimulation waveform comprising a pulse portion having a first polarity and a subsequent recharge portion having a second polarity that is opposite to the first polarity. The coupling circuit comprises a first node connected to the electrical stimulation generator, a second node configured to deliver the biphasic electrical stimulation waveform to the patient, and a capacitor. The coupling circuit is configured to operate in a first state to couple the capacitor between the first and second nodes in a first orientation and operate in a second state to couple the capacitor between the first and second nodes in a second orientation that is opposite to the first orientation. The processing module is configured to set the state of the coupling circuit to one of the first and second states and transition the coupling circuit between the first and second states during the pulse portion to maintain a voltage across the capacitor within a threshold voltage range.

In some examples, a device for delivering electrical stimulation to a patient according to the present disclosure comprises an electrical stimulation generator, N coupling circuits, and a processing module. Each of the N coupling circuits comprises a first node connected to the electrical stimulation generator, a second node configured to deliver electrical stimulation to a patient, and a capacitor. Each of the N coupling circuits are configured to operate in a first state to couple the capacitor between the first and second nodes in a first orientation and operate in a second state to couple the capacitor between the first and second nodes in a second orientation that is opposite to the first orientation. The processing module is configured to set the state of each of the N coupling circuits to one of the first and second states.

In some examples, a device for delivering electrical stimulation to a patient comprises means for generating electrical stimulation and means for capacitively coupling the generated electrical stimulation to the patient using a capacitor. The means for capacitively coupling comprises means for orienting the capacitor in a first orientation during delivery of the generated electrical stimulation to the patient and means for orienting the capacitor in a second orientation during delivery of the generated electrical stimulation to the patient, wherein the second orientation is opposite to the first orientation. Additionally, the device comprises means for setting the orientation of the capacitor to one of the first and second orientations during delivery of the generated electrical stimulation.

In some examples, a method for delivering electrical stimulation to a patient comprises generating electrical stimulation and capacitively coupling the generated electrical stimulation to the patient using a capacitor. Capacitively coupling the generated electrical stimulation comprises orienting the capacitor in a first orientation during delivery of the generated electrical stimulation to the patient and orienting the capacitor in a second orientation during delivery of the generated electrical stimulation to the patient, wherein the second orientation is opposite to the first orientation. Additionally, the method comprises setting the orientation of the capacitor to one of the first and second orientations during delivery of the generated electrical stimulation.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 4A and 4B show current sources delivering stimulation to a patient modeled as a resistor.

DETAILED DESCRIPTION

Figure 1:
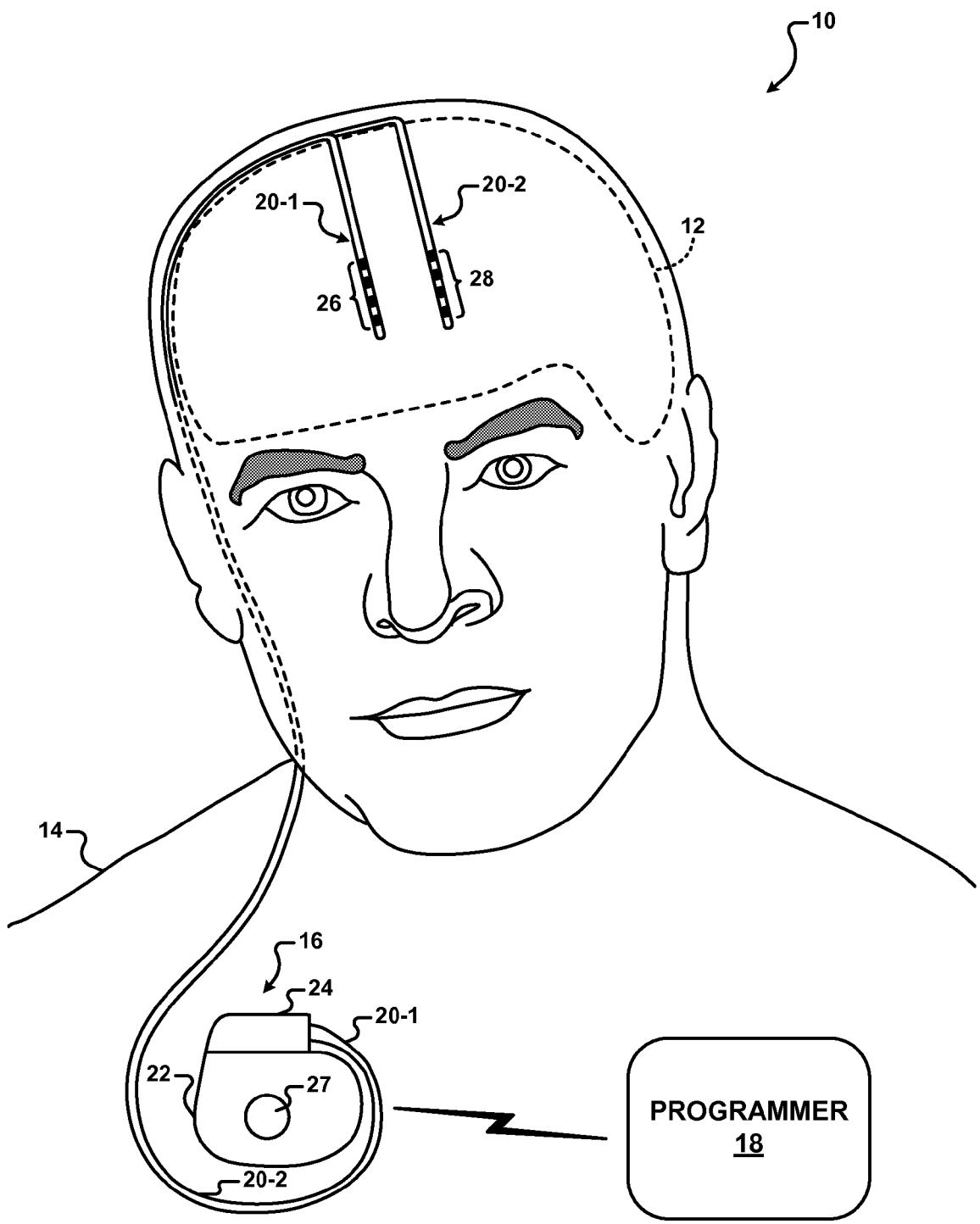
FIG. 1 is a conceptual diagram illustrating an example therapy system that is implanted proximate to a brain of a patient in order to help manage a patient condition.

Electrical stimulation devices, such as neurostimulation devices, may include a stimulation generator that delivers electrical stimulation to a patient via one or more electrodes. The stimulation generator may be capacitively coupled to each of the electrodes using separate capacitors that function to remove low frequency (e.g., DC) components of the electrical stimulation delivered to the patient. The physical dimensions and types of capacitors used in an electrical stimulation device may be selected based on the application in which the electrical stimulation device will be used. In some examples, the capacitors may be selected based on the amount of energy delivered during stimulation. In general, greater amounts of stimulation energy may require larger capacitors.

The physical size of the capacitors used to couple the stimulation generator to the electrodes may prevent miniaturization of the stimulation device. In one example, some electrical stimulation devices may include a large number of such capacitors (e.g., 16-32), which may tend to increase the amount of space used by the capacitors within the electrical stimulation device. In other examples, electrical stimulation devices that generate larger energy stimulation pulses may include larger capacitors that may tend to require a greater amount of space within the stimulation device.

In some examples, an electrical stimulation device of the present disclosure includes coupling circuits that capacitively couple a stimulation generator of the stimulation device to the electrodes of the stimulation device. The coupling circuit of the present disclosure may be configured to attenuate low frequency components (e.g., DC components) of the electrical stimulation waveform generated by the stimulation generator for delivery to an electrode. The coupling circuit described herein may provide several advantages relative to other coupling techniques used in electrical stimulation. For example, the coupling capacitors of the coupling circuit may permit miniaturization relative to capacitors used in other coupling techniques. That is, in some examples, the coupling capacitors may be reduced in size. In some examples, the coupling capacitors described herein may be implemented as miniaturized discrete capacitor components or integrated circuit capacitors. Implementation of such miniaturized coupling capacitors in a stimulation device may allow for miniaturization of the stimulation device itself and also the inclusion of a greater number of coupling capacitors within the stimulation device without requiring a substantial increase or any increase in the size of the stimulation device.

In some examples, a single coupling circuit of the present disclosure may be connected between the stimulation generator of the stimulation device and a single electrode of the stimulation device. For example, when the stimulation generator includes a current source that delivers stimulation to a patient, the coupling circuit may be connected between the current source and the electrode that delivers stimulation to the patient. In examples where the stimulation generator includes a voltage source that delivers stimulation to the patient, the coupling circuit may be connected between the voltage source and the electrode that delivers stimulation to the patient.

In some examples, each of the electrodes may be coupled to a corresponding coupling circuit. For example, stimulation devices that deliver electrical stimulation to N electrodes may include N coupling circuits that, respectively, couple the stimulation generator to the N electrodes. In other examples, if the stimulation device is configured to deliver electrical stimulation to N electrodes, the device may include less than N coupling circuits, some or all of which may be multiplexed to the N electrodes.

The coupling circuit may include a first node that receives electrical stimulation generated by the stimulation generator. For example, the first node may be electrically connected to the stimulation generator. The coupling circuit may include a second node that is configured to connect to a conductor that delivers therapy to a patient. For example, the second node may be electrically connected to an output terminal of the electrical stimulation device that is configured to receive a lead which terminates at an electrode. Accordingly, the second node may be configured to deliver electrical stimulation to the patient via an electrode.

A coupling circuit constructed in accordance with the present disclosure may include a coupling capacitor and a plurality of switches arranged between the first and second nodes of the coupling circuit. The coupling circuit may be configured in a variety of different states, depending on the state of the switches. As described herein, the switches may be in either an open state (e.g., an open circuit) or a closed state (e.g., a short circuit). The coupling circuit may act as an open circuit in one state. In other examples, the switches may be configured to connect the coupling capacitor between the first and second nodes in order to capacitively couple the first and second nodes. The operating states of a coupling circuit are described hereinafter.

The stimulation device may include a processing module that controls the states of the switches included in the coupling circuit in order to control the state of the coupling circuit. In one example, the processing module may configure the coupling circuit to act as an open circuit, e.g., by opening all the switches of the coupling circuit. In examples where the coupling circuit acts as an open circuit, the stimulation generator may be disconnected from the electrode. In other examples, the processing module may configure the coupling circuit such that the coupling capacitor is connected between the first and second nodes, e.g., by selectively closing some of the switches of the coupling circuit. Such a connection may capacitively couple the first and second nodes, and, therefore, capacitively couple the stimulation generator to the electrode.

The coupling circuit may be configured to connect the coupling capacitor between the first and second nodes in one of two orientations. The coupling circuit may be referred to as operating in a "first coupling state" when the coupling capacitor is connected between the first and second nodes in a first orientation. The coupling circuit may be referred to as operating in a "second coupling state" when the coupling capacitor is connected between the first and second nodes in a second orientation.

As described herein, an orientation of the capacitor may refer to how the terminals of the capacitor are connected between the first and second nodes. In general, a capacitor may have first and second terminals that are each connected to electrodes which are separated by a dielectric material. The capacitor may be connected in a first orientation between the first and second nodes when the first terminal of the capacitor is connected to the first node, and the second terminal of the capacitor is connected to the second node of the coupling circuit. Alternatively, the capacitor may be connected in the second orientation between the first and second nodes of the coupling circuit when the second terminal of the capacitor is connected to the first node and the first terminal of the capacitor is connected to the second node of the coupling circuit.

In order to configure the coupling circuit in the first coupling state, the processing module may set the states of the switches such that the coupling capacitor is connected between the first and second nodes in the first orientation. In order to configure the coupling circuit in the second coupling state, the processing module may set the states of the switches such that the coupling capacitor is connected between the first and second nodes in the second orientation. As illustrated and described herein, the first node of the coupling circuit may be connected to the stimulation generator and the second node may be connected to the electrode. Accordingly, in the first coupling state, the coupling capacitor may be connected between the stimulation generator and the electrode in the first orientation. Similarly, in the second coupling state, the coupling capacitor may be connected between the stimulation generator and the electrode in the second orientation.

The coupling circuit may also be described in terms of how the coupling capacitor is connected to the first and second nodes via the switches. When the coupling circuit is set to the first coupling state, the stimulation generator may be connected to the first terminal of the coupling capacitor through a closed switch while the second terminal of the coupling capacitor may be connected to the electrode through another closed switch. When the coupling circuit is set to the second coupling state, the stimulation generator may be connected to the second terminal of the coupling capacitor through a closed switch while the first terminal of the capacitor may be connected to the electrode through another closed switch.

In summary, the processing module may set the state of the switches of the coupling circuit in order to disconnect the electrode from the stimulation generator or in order to couple an electrode to the simulation generator via a coupling capacitor. The processing module may selectively configure the coupling circuit to connect the capacitor between the stimulation generator in one of two different orientations, depending on which switches of the coupling circuit are closed by the processing module. In both the first and second coupling states, the capacitor may be connected at one node to the stimulation generator and connected to the electrode at the other node such that the capacitor filters out low frequency components of the electrical stimulation delivered by the stimulation generator. In the first coupling state, the processing module may set the states of the switches such that the first terminal of the capacitor is connected to the stimulation generator and the second terminal of the capacitor is connected to the electrode. In the second coupling state, the processing module may set the states of the switches such that the second terminal of the capacitor is connected to the stimulation generator and the first terminal of the capacitor is connected to the electrode.

Figures 5A, 5B:
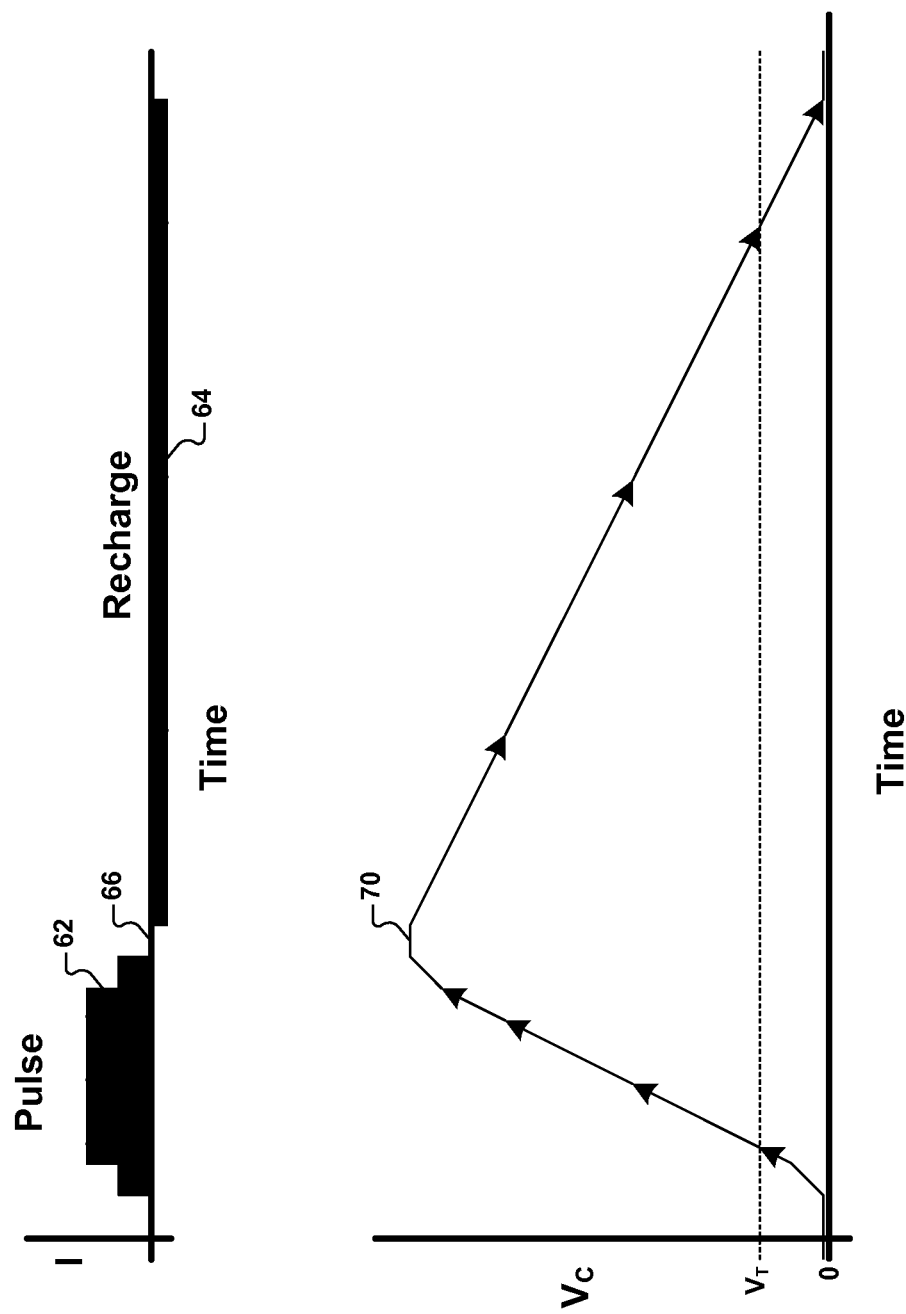
FIG. 5A shows a biphasic current waveform delivered by adjustable current sources.
FIG. 5B shows a voltage waveform developed across the capacitors of FIGS. 4A and 4B during delivery of a biphasic current waveform.
Figure 14:
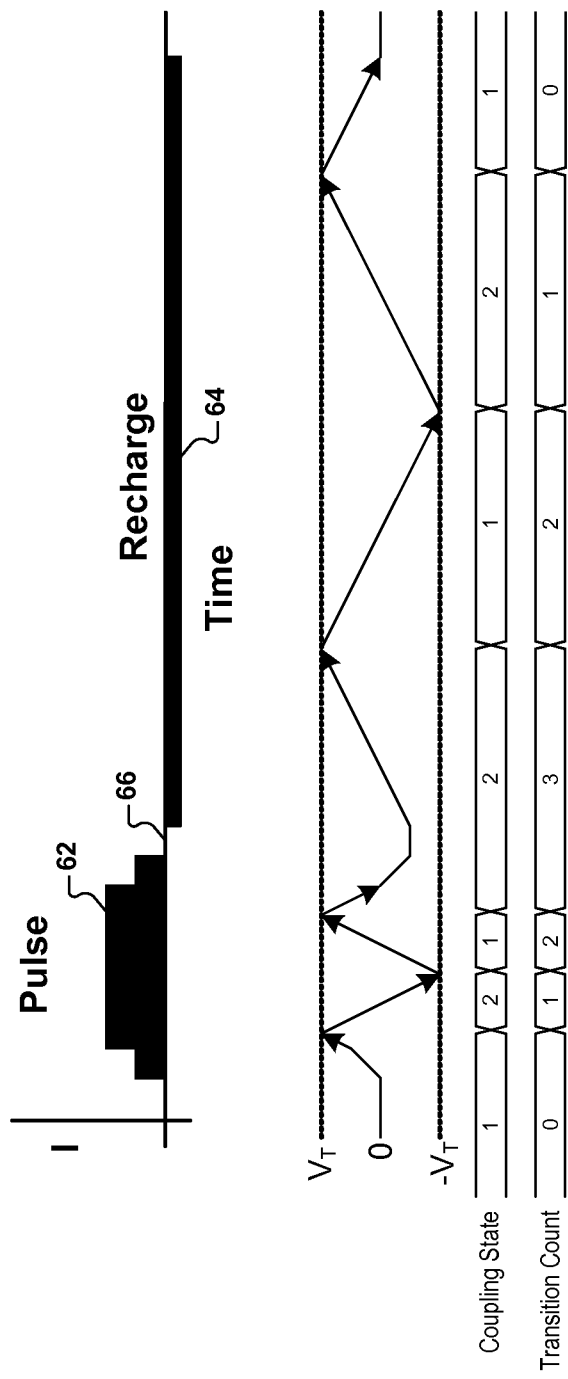
FIG. 14 shows the voltage across a coupling capacitor of FIGS. 12A-13B during delivery of a biphasic waveform.

The processing module may control the stimulation generator to deliver electrical stimulation via the coupling circuit. For example, the processing module may control the stimulation generator based on stimulation parameters stored in memory of the stimulation device. As described herein, the processing module may control the stimulation generator to deliver a biphasic waveform (e.g., a charge-balanced biphasic waveform). The biphasic waveform may include an initial pulse portion, an interval during which stimulation is ceased, then a recharge waveform. In some examples, a charge-balanced biphasic waveform may deliver the same amount of charge to the patient during the recharge waveform of the biphasic waveform as was delivered during the pulse portion of the biphasic waveform. Example biphasic waveforms are illustrated in FIGS. 5A and 14.

The processing module may control delivery of the biphasic waveform according to the stimulation parameters stored in memory. While the biphasic waveform is being delivered, the processing module may control the state of the coupling circuit based on the voltage across the coupling capacitor, as detected by a voltage detection module. The processing module may, for example, control the coupling circuit in order to maintain the voltage across the coupling capacitor within a threshold range of voltages, described herein as a positive threshold voltage ($V_T$) and a negative threshold voltage ($-V_T$).

The processing module may put the coupling circuit in the first coupling state before starting the pulse portion of the biphasic waveform. After setting the coupling circuit to the first coupling state, the processing module may control the stimulation generator to start the biphasic waveform. The coupling capacitor, which is in the first orientation, may eventually charge to the positive threshold voltage $V_T$ during delivery of the pulse. The processing module may determine when the voltage across the coupling capacitor has reached the positive threshold voltage $V_T$ during delivery of the pulse portion.

The processing module may transition the coupling circuit from the first coupling state to the second coupling state when the voltage across the coupling capacitor reaches the positive threshold voltage $V_T$ (e.g., in response to determining that the voltage across the coupling capacitor has reached the positive threshold voltage $V_T$). The voltage across the coupling capacitor, which is in the second orientation in the second coupling state, may tend towards zero volts and eventually towards the negative threshold voltage $-V_T$. The processing module may then determine when the voltage across the coupling capacitor has reached the negative threshold voltage $-V_T$ during delivery of the pulse portion.

The processing module may transition the coupling circuit from the second coupling state back to the first coupling state when the voltage across the coupling capacitor reaches the negative threshold voltage $-V_T$ (e.g., in response to determining that the voltage across the coupling capacitor has reached the negative threshold voltage $-V_T$). The processing module may continue to transition the state of the coupling circuit during delivery of the pulse portion of the waveform until the pulse has been delivered to the patient. The processing module may also transition the state of the coupling circuit during delivery of the recharge waveform of the biphasic waveform in a similar manner.

The transitioning of the capacitor orientation within the coupling circuit may prevent the voltage across the coupling capacitor from reaching a voltage that is greater than a threshold voltage. In other words, the processing module may control the state of the coupling circuit such that the voltage across the coupling capacitor is maintained within a threshold voltage range. Put another way, the processing module may flip the orientation of the coupling capacitor between the stimulation generator and the electrode during stimulation to maintain the amount of charge on the coupling capacitor within a threshold range of charge. Since the stimulation device of the present disclosure may limit the amount of charge stored on the coupling capacitors, the coupling capacitors of the present disclosure may be miniaturized.

In some examples, a stimulation device including the coupling circuits of the present disclosure may be used in a variety of different electrical stimulation applications, regardless of the amount of stimulation energy to be delivered to a patient. For example, since the maximum amount of charge allowed on the coupling capacitors of the coupling circuits may be selectively limited, the coupling capacitors may be used in a wide range of different stimulation applications, regardless of the amount of charge to be delivered to the patients. Accordingly, a stimulation device including the coupling circuits may find application in a wide variety of different types of stimulation applications independent of the pulse energies used in those applications.

In other aspects of the present disclosure, the processing module may control the stimulation generator and the coupling circuit in order to deliver a charge-balanced biphasic waveform. A biphasic waveform may include a pulse portion having a first polarity and a subsequently delivered recharge portion having a second polarity that is opposite to the first polarity. Initially, before starting delivery of the pulse portion, the voltage across the coupling capacitor may be 0 volts (V). During delivery of the pulse portion, the processing module may maintain a count of the number of transitions of the coupling circuit. The count may be representative of the total amount of charge that was stored on the coupling capacitor during the pulse portion of the biphasic waveform. Then, during subsequent delivery of the recharge waveform, the processing module may decrement the count for each of the transitions of the coupling circuit. Upon reaching zero, the number of transitions (i.e., charges of the capacitor) during the pulse and the recharge waveform are equal. The processing module may then instruct the stimulation generator to cease stimulation when the voltage across the coupling capacitor is equal to 0V since the delivery of the biphasic waveform may be charged-balanced at that time, assuming the coupling capacitor was uncharged prior to delivery of the biphasic waveform.

FIG. 1 is a conceptual diagram illustrating an example therapy system 10 that is implanted proximate to brain 12 of patient 14 in order to help manage a patient condition, such as pain, psychiatric disorder, movement disorder, or seizure disorder. Therapy system 10 includes implantable medical device (IMD) 16, a medical device programmer 18, and leads 20-1, 20-2 (collectively "leads 20").

IMD 16 includes a housing 22 configured for implantation within patient 14. Although IMD 16 is configured for implantation within patient 14, in other examples, the techniques of the present disclosure may be implemented in an electrical stimulation device that is external to patient 14. Connector block 24 is coupled to housing 22. Connector block 24 is configured to receive leads 20. Leads 20 are coupled to IMD 16 via connector block 24, e.g., using set screws. Leads 20 each include conductors that extend along the length of leads 20 and terminate at electrodes 26, 28. Connector block 24 may include electrical contacts configured to contact conductors of leads 20. The electrical contacts of connector block 24 may electrically couple electrodes 26, 28 to electronics of IMD 16. In some examples, IMD 16 may include a housing electrode 27.

Although two leads 20-1, 20-2 are illustrated in FIG. 1, techniques of the present disclosure may be applicable to IMDs having more or less than two leads. Although IMD 16 is illustrated as delivering electrical stimulation to four electrodes per lead, the techniques of the present disclosure may be applicable to IMDs having more or less than four electrodes per lead. For example, the techniques of the present disclosure may be applicable to IMDs that deliver stimulation via 16-32 electrodes, or more.

IMD 16 includes a stimulation generator 30 that delivers electrical stimulation to one or more regions of brain 12 via electrodes 26, 28 on leads 20. In the example shown in FIG. 1, therapy system 10 may be referred to a deep brain stimulation (DBS) system because IMD 16 provides electrical stimulation therapy to tissue within brain 12, e.g., a tissue site under the dura mater of brain 12. Leads 20 may be positioned to deliver electrical stimulation to one or more target tissue sites within brain 12 to manage patient symptoms associated with the patient disorder. In the example shown in FIG. 1, leads 20 are implanted within the right and left hemispheres, respectively, of brain 12 in order to deliver electrical stimulation to one or more regions of brain 12, which may be selected based on many factors, such as the type of patient condition for which therapy system 10 is implemented to manage.

Although a DBS system is illustrated in the disclosure, it is contemplated that the techniques of the present disclosure may be implemented in other types of electrical stimulation applications used to treat various types of patient conditions. For example, the techniques of the present disclosure may be implemented in spinal cord stimulation systems, gastric stimulation systems, or systems that electrically stimulate any other suitable nerve, organ, muscle, or muscle group to treat a condition of patient 14. Although therapy system 10 may be used to treat conditions such as movement disorders or other neurological disorders, it is contemplated that the techniques of the present disclosure may be implemented in devices used to treat other types of patient conditions, such as pain, urinary or fecal incontinence, or obesity, for example.

IMD 16 generates the electrical stimulation according to one or more therapy parameters, which may be arranged in a therapy program (or a parameter set) stored in memory of IMD 16. IMD 16 may deliver electrical stimulation according to a variety of different parameters, such as voltage or current pulse amplitude, pulse rate, and pulse width. Electrical stimulation parameters may define a variety of different waveforms, such as rectangular waveforms, sinusoidal waveforms, ramped signals, etc. In addition, if different electrodes are available for delivery of stimulation, the electrical stimulation parameters may define different electrode combinations, which can include selected electrodes and their respective polarities.

External programmer 18 wirelessly communicates with IMD 16 to provide or retrieve therapy information. Programmer 18 is an external computing device that the user, e.g., the clinician and/or patient 14, may use to communicate with IMD 16. For example, programmer 18 may be a clinician programmer that the clinician uses to communicate with IMD 16 and program one or more therapy programs for IMD 16. Alternatively, programmer 18 may be a patient programmer that allows patient 14 to select programs and/or view and modify therapy parameters.

Figure 2:
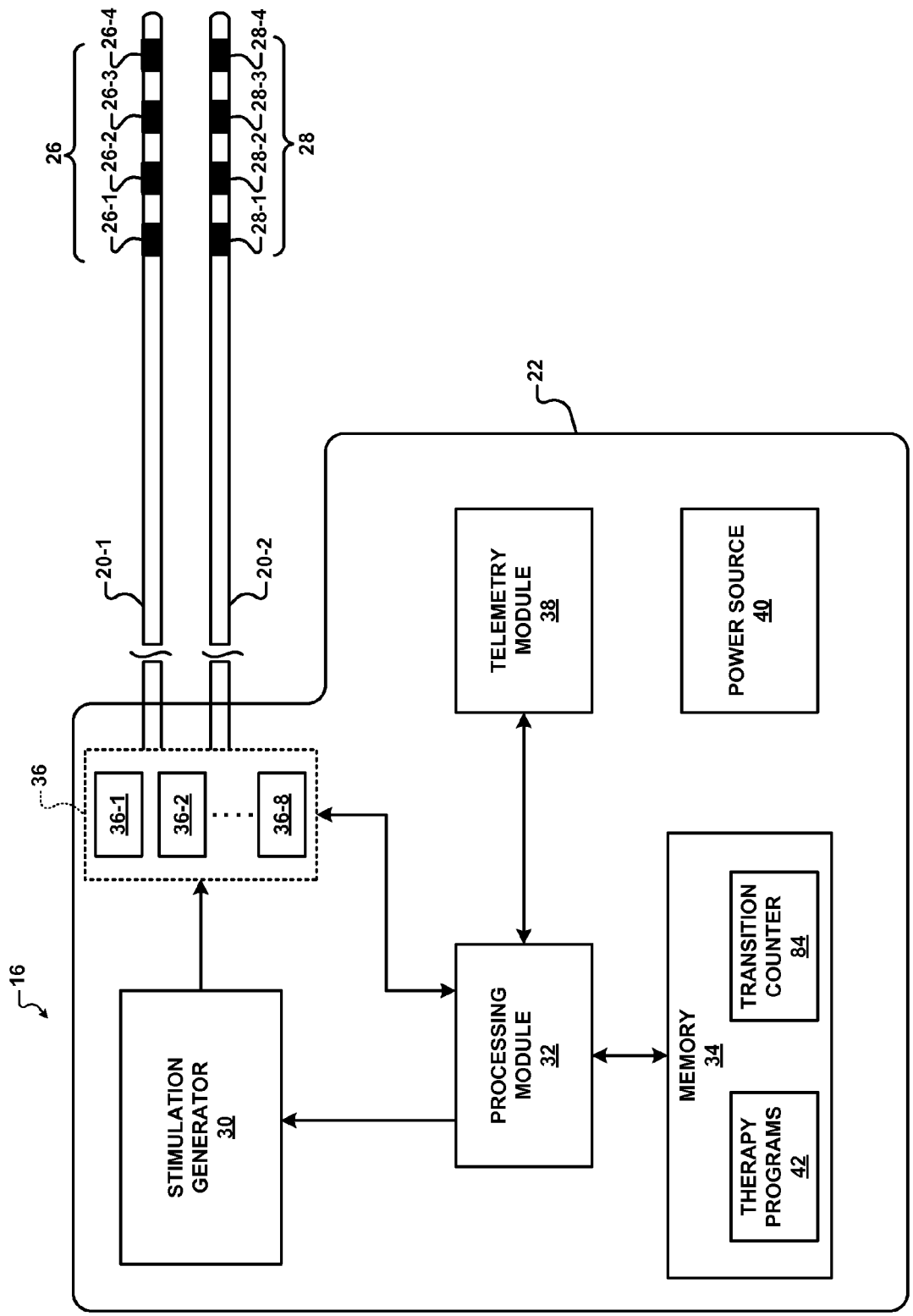
FIG. 2 is a functional block diagram illustrating components of an example implantable medical device.

FIG. 2 is a functional block diagram illustrating components of example IMD 16. In the example shown in FIG. 2, IMD 16 includes a processing module 32, memory 34, stimulation generator 30, coupling circuits 36-1, 36-2, ..., and 36-8 (collectively "coupling circuits 36"), telemetry module 38, and power source 40. In some examples, IMD 16 may include a sensor (not shown), such as a motion sensor (e.g., an accelerometer), that generates a signal indicative of patient activity (e.g., patient movement or patient posture transitions).

Processing module 32, coupling circuits 36, stimulation generator 30, memory 34, and telemetry module 38 represent functionality that may be included in IMD 16 of the present disclosure. Processing module 32, coupling circuits 36, stimulation generator 30, memory 34, and telemetry module 38 of the present disclosure may include any discrete and/or integrated electronic circuit components that implement analog and/or digital circuits capable of producing the functions described herein. For example, processing module 32, coupling circuits 36, stimulation generator 30, memory 34, and telemetry module 38 may include analog circuits, e.g., amplification circuits, filtering circuits, and/or other signal conditioning circuits. Processing module 32, coupling circuits 36, stimulation generator 30, memory 34, and telemetry module 38 may also include digital circuits, e.g., combinational or sequential logic circuits, memory, etc. Memory 34 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory 34 may include instructions that, when executed by one or more processing circuits, cause processing module 32, coupling circuits 36, stimulation generator 30, and telemetry module 38 to perform various functions described herein.

The functions attributed to processing module 32, coupling circuits 36, stimulation generator 30, memory 34, and telemetry module 38 herein may be embodied as one or more processors, hardware, firmware, software, or any combination thereof. Depiction of different features as separate components is intended to highlight different functional aspects and does not necessarily imply that such components must be realized by separate hardware or software components. Rather, functionality associated with one or more components may be performed by separate hardware or software components, or integrated within common or separate hardware or software components.

In the example shown in FIG. 2, memory 34 may store therapy programs 42. A therapy program may define electrical stimulation parameters, such as a stimulation electrode combination, electrode polarity, current or voltage amplitude values, and, if stimulation generator 30 generates and delivers stimulation pulses, the therapy programs may define values for a pulse width, pulse rate, and duty cycle of a stimulation signal. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. As described herein, stimulation generator 30 may generate a biphasic waveform. Example stimulation parameters stored in memory 34 that may define the biphasic waveform may include pulse amplitude (voltage and/or current), pulse width, interval duration, recharge waveform amplitude (voltage and/or current), and recharge waveform width.

IMD 16 is coupled to leads 20-1 and 20-2, which include electrodes 26-1, 26-2, 26-3, and 26-4 (collectively "electrodes 26") and electrodes 28-1, 28-2, 28-3, and 28-4 (collectively "electrodes 28"). Electrodes 26, 28 are electrically coupled to stimulation generator 30 via conductors within the respective leads 20 and coupling circuits 36. For example, each of electrodes 26, 28 may be coupled to a different coupling circuit. Each of electrodes 26, 28 may be coupled to separate conductors so that electrodes 26, 28 may be individually selected, or in some examples, two or more electrodes 26 and/or two or more electrodes 28 may be coupled to a common conductor.

Processing module 32 controls stimulation generator 30 to generate and deliver electrical stimulation signals to patient 14 according to selected therapy parameters. For example, processing module 32 may control stimulation generator 30 according to therapy programs 42 stored in memory 34 to apply particular stimulation parameter values such as current or voltage amplitude. Stimulation generator 30 may be a single channel or a multi-channel stimulation generator. In particular, stimulation generator 30 may be capable of delivering, a single stimulation pulse, multiple stimulation pulses or a continuous signal at a given time via a single electrode combination or multiple stimulation pulses at a given time via multiple electrode combinations. In examples in which stimulation generator 30 is a single channel stimulation generator, stimulation generator 30 is configured to output electrical stimulation signals via a single channel. In examples in which stimulation generator 30 is a multi-channel stimulation generator, stimulation generator 34 is configured to output electrical stimulation signals via a single channel (e.g., via a single electrode combination) or via multiple channels (e.g., via multiple electrode combinations) at different times (e.g., on a time-interleaved basis) or simultaneously using a single stimulation engine or multiple stimulation engines.

In some examples, stimulation generator 30 includes a plurality of stimulation engines that provide a current source and a current sink for each electrode 26, 28 electrically coupled to IMD 16 to be driven by the stimulation engines. In examples in which stimulation generator 30 is configured to deliver current-controlled electrical stimulation, processing module 32 may be configured to control the stimulation engines to selectively source or sink current via each electrode at a variety of current amplitudes. In other examples, stimulation generator 30 may be configured to deliver voltage-controlled electrical stimulation.

In other examples, stimulation generator 30 includes a fewer number of stimulation engines, e.g., one or more stimulation engines are shared for two or more electrodes, and IMD 16 includes a switch module, and processing module 32 may be configured to control the switch module to apply the stimulation signals generated by stimulation generator 30 to selected combinations of electrodes 26, 28. The switch module may be, for example, a switch array, switch matrix, multiplexer, or any other type of switching module configured to selectively couple stimulation energy to selected electrodes 26, 28. In some examples in which IMD 16 includes a switch module, stimulation generator 30 and the switch module may be configured to deliver multiple channels on a time-interleaved basis. For example, the switch module may serve to time divide the output of stimulation generator 30 across different electrode combinations at different times to deliver multiple programs or channels of stimulation energy to patient 12.

Telemetry module 38 supports wireless communication between IMD 16 and programmer 18 or another computing device. Processing module 32 of IMD 16 may receive, as updates to programs, values for various stimulation parameters such as amplitude and electrode combination, from programmer 18 via telemetry module 38. The updates to the therapy programs may be stored within memory 34.

Power source 40 delivers operating power to various components of IMD 16. Power source 40 may include a small rechargeable or non-rechargeable battery and a power generation circuit to produce the operating power. In some examples, stimulation generator 30 may include a circuit that boosts the voltage output by power source 40. The boosted voltage may be used by stimulation generator 30 to generate current and/or voltage delivered to patient 14. In examples where stimulation generator 30 includes a circuit that boosts voltage, processing module 32 may control the level of voltage provided by the circuit.

Coupling circuits 36 include circuit components that capacitively couple stimulation generator 30 to electrodes 26, 28. Each of coupling circuits 36 may include a coupling capacitor and a plurality of switches. Each of coupling circuits 36 may be associated with a different one of electrodes 26, 28. For example, IMD 16 may have separate conductive terminals that may be connected to each of coupling circuits 36. When leads 20 are connected to IMD 16, each of the separate conductive terminals may receive a different conductor of leads 20. Accordingly, each of the separate conductive terminals of IMD 16 may be associated with one of electrodes 26, 28 when leads 20 are connected to IMD 16. As illustrated in FIG. 2, IMD 16 may include eight separate coupling circuits 36, each of which are coupled to corresponding to electrodes 26, 28.

In other examples, IMD 16 may be a leadless stimulator (e.g., a microstimulator) with one or more arrays of electrodes arranged on a housing of the stimulator in addition to, or instead of, leads 20 that extend from the outer housing of IMD 16. The devices, systems, and techniques described herein may also be applicable to the leadless stimulator, which may also be referred to as a leadless stimulation device. For example, an example leadless stimulator may include a stimulator generator and a plurality of coupling circuits that capacitively couple the stimulation generator of the leadless stimulator to the electrodes of the leadless stimulator, e.g., using the configuration and techniques described herein. The leadless stimulator may include, for example, processing module 32, stimulation generator 30, memory 34, coupling circuits 36, telemetry module 38, and power source 40. However, coupling circuits 36 may be connected to electrodes on an outer housing of the leadless stimulator via conductors internal to the housing or embedded in the housing.

Figure 3:
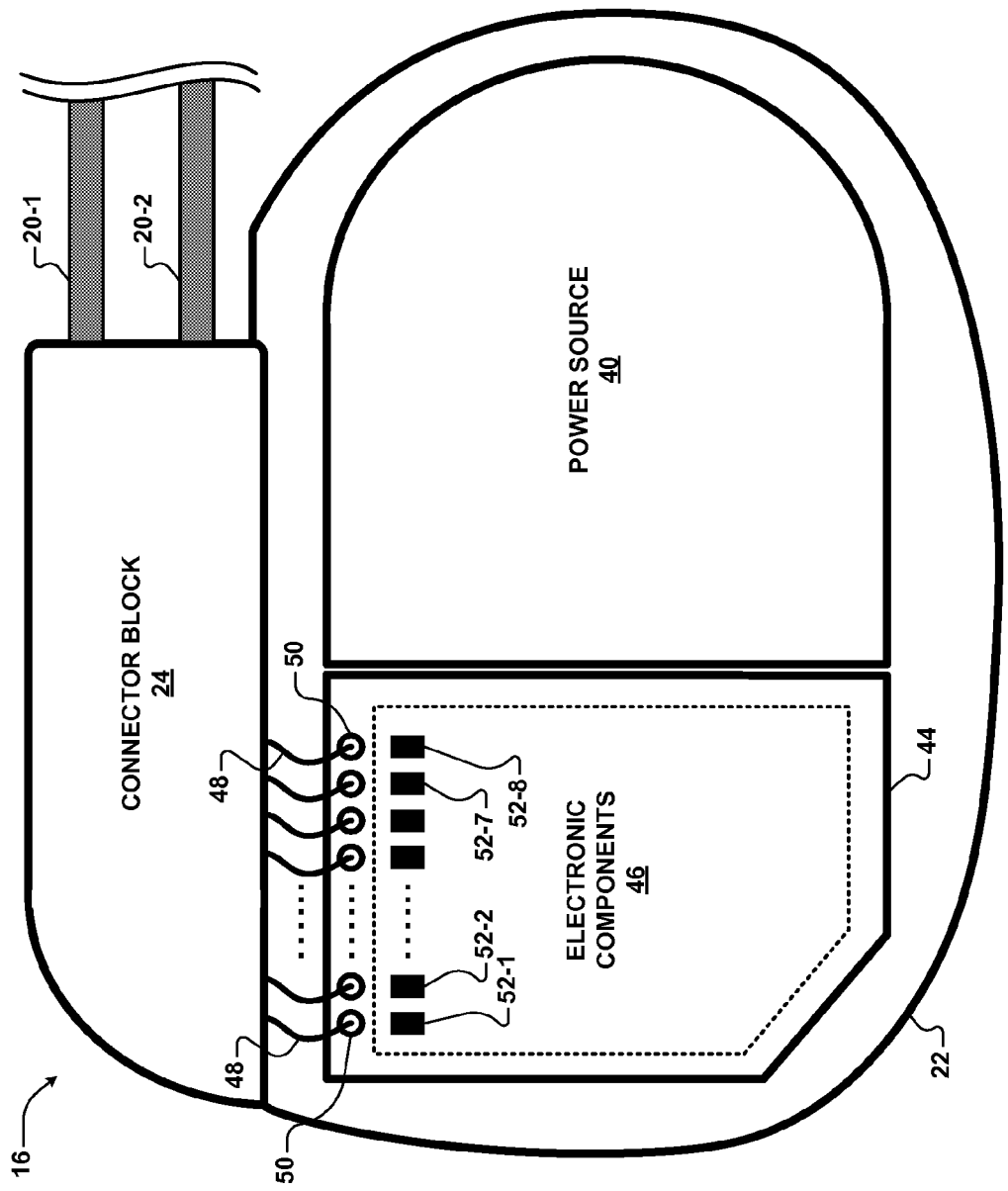
FIG. 3 shows components of an example implantable medical device.

FIG. 3 shows components of IMD 16 within housing 22. Components of IMD 16 include power source 40, a printed circuit board (PCB) 44, and electronic components 46. PCB 44 includes electronic components 46 of IMD 16. Electronic components 46 include, but are not limited to, processing module 32, coupling circuits 36, stimulation generator 30, memory 34, and telemetry module 38. PCB 44 may represent a structure within IMD 16 that is used to mechanically support and electrically connect electronic components 46 within housing 22. In some examples, PCB 44 may include one or more layers of conductive traces and conductive vias that provide electrical connection between electronic components 46.

PCB 44 may provide electrical connections between power source 40 and electronic components 46 such that power source 40 provides power to electronic components 46. Leads 20 may be connected to electronic components 46 on PCB 44 through connecting wires 48. For example, connecting wires 48 may be connected to conductors of leads 20 at one end, and connected to PCB connection points 50 on PCB 44 at the other end. PCB connection points 50 are electrically connected to electronic components 46, providing electrical connection between electronic components 46 of IMD 16 and conductors within leads 20. For example, PCB connection points 50 are connected to coupling circuits 36 (FIG. 2). In examples where stimulation generator 30 is providing electrical stimulation to patient 14 via one of electrodes 26, 28, stimulation generator 30 may be capacitively coupled to a connection point associated with that electrode via the coupling circuit associated with that electrode.

As illustrated in FIG. 3, capacitors 52-1, 52-2, ..., and 52-8 (collectively "capacitors 52") included in coupling circuits 36 may be laid out on PCB 44. In some examples, the techniques of the present disclosure may allow for miniaturization of coupling capacitors 52 because the amount of charge stored on coupling capacitors 52 may be reduced relative to capacitors used in typical stimulation circuits such as those illustrated in FIGS. 4A and 4B. In some examples, coupling circuits 36 may be fabricated as an integrated circuit, which may allow for a further miniaturization of coupling circuits 36, and, therefore, further miniaturization of IMD 16.

FIGS. 4A and 4B show a circuit that capacitively couples electrodes to a stimulation generator using capacitors 54-1, 54-2 instead of coupling circuits 36 of the present disclosure. As illustrated and described hereinafter with respect to FIGS. 6-16, coupling circuits 36 of the present disclosure may provide various advantages relative to capacitors 54-1, 54-2 used in FIGS. 4A-4B. Operation of the circuits of FIGS. 4A-4B in response to delivery of a biphasic waveform is now described. Subsequently, the operation and various advantages of IMD 16 of the present disclosure including coupling circuits 36 are described with reference to FIGS. 6-16.

As described above, power source 40 may provide power to stimulation generator 30 for generation of electrical stimulation. In some examples, stimulation generator 30 may include a voltage boosting circuit in order to generate a sufficient voltage for delivery of electrical stimulation. The electrical schematics included in FIGS. 4A-4B, 6-13B, and 15 include power rails 56-1, 56-2 that provide power to stimulation generator 30, e.g., current sources and/or voltage sources of stimulation generator 30. Power rails 56-1, 56-2 may receive the voltage generated by power source 40 in some examples. In other examples, power rails 56-1, 56-2 may receive a boosted voltage from a voltage boosting circuit that boosts the voltage generated by power source 40. As described above, processing module 32 may control the voltage boosting circuit during delivery of electrical stimulation. Power rails 56-1, 56-2 may provide voltages of different polarities and magnitudes depending on the implementation. In some examples, power rail 56-1 may provide a positive voltage relative to power rail 56-2. In other examples, power rail 56-1 may provide a negative voltage relative to power rail 56-2. Example voltages provided by power rails 56-1, 56-2 may include a voltage range from 1-20V in some examples.

In FIGS. 4A and 4B, adjustable current sources 58-1, 58-2, 58-3, 58-4 (collectively "adjustable current sources 58") deliver stimulation to a patient, modeled by resistor 60. Current sources 58-2, 58-3, illustrated by dotted lines, may be turned off in FIG. 4A. In other words, current sources 58-2, 58-3 may act as open circuits in FIG. 4A. Current sources 58-1, 58-4, illustrated by dotted lines, may be turned off in FIG. 4B. In other words, current sources 58-1, 58-4 may act as open circuits in FIG. 4B. FIG. 5A shows a biphasic current waveform delivered by adjustable current sources 58. FIG. 5B shows the voltage $V_C$ with respect to time that is developed across capacitors 54-1, 54-2 during delivery of the biphasic current waveform.

The biphasic waveform of FIG. 5A includes a first waveform portion 62 having a first stimulation polarity (e.g., a positive polarity) and a second waveform portion 64 having a second stimulation polarity (e.g., a negative polarity) that is opposite to the first stimulation polarity. In some examples, the biphasic waveform may include an interval 66 during which electrical stimulation is ceased (e.g., brought to, or near, a value of 0 A or 0V). The biphasic waveform of FIG. 5A is reproduced in FIG. 14 along with a voltage waveform and other information used to describe operation of IMD 16 of the present disclosure with reference to FIGS. 6-16.

The first waveform portion 62 of the biphasic waveform of FIG. 5A may be referred to herein as a pulse portion of the biphasic waveform, or simply as a "pulse 62." FIG. 4A illustrates delivery of pulse 62 by adjustable current sources 58. Electrodes 68-1, 68-2 are illustrated as delivering a current pulse (I) to tissue of a patient, modeled as resistor 60. Adjustable current sources 58-1, 58-4 are illustrated as delivering pulse 62. Adjustable current sources 58-2, 58-3 are turned off (e.g., act as open circuits) during delivery of pulse 62. During delivery of pulse 62, voltage $V_C$ builds up across capacitor 54-1. The voltage $V_C$, with respect to time, is illustrated in FIG. 5B. As illustrated in FIG. 5B, the voltage $V_C$ monotonically builds up to a peak voltage 70 during delivery of pulse 62 until stimulation is ceased during interval 66.

FIG. 5B also illustrates an example positive threshold voltage $V_T$, which may correspond to the maximum voltage to which capacitors 52 of coupling circuits 36 are charged, as described hereinafter. As illustrated in FIG. 5B, peak voltage 70 may be much larger than the threshold voltage $V_T$, depending on the size of capacitors used. The relatively large peak amount of charge stored at peak voltage 70 may require relatively large capacitors 54-1, 54-2 to be used in the circuits of FIGS. 4A-4B, whereas the smaller charge stored in coupling circuit 36 of the present disclosure may allow the physical size of coupling capacitors 52 to be reduced relative to a capacitors 54-1, 54-2 used in the circuits of FIGS. 4A-4B. Reduction in the size of coupling capacitors 52 may allow for miniaturization of IMD 16 as a whole, and inclusion of more coupling capacitors within a smaller IMD when more electrodes are used. In some examples of this disclosure, since the voltage developed across the coupling capacitors of the coupling circuits (e.g., 36-1, 36-2) may be reduced relative to typical stimulation circuits (e.g., in FIGS. 4A-4B), the amount of voltage boost used to generate stimulation in IMD 16 of the present disclosure may be reduced. Such a reduction in the amount of voltage boost may provide power savings.

Subsequent to delivering pulse 62, current sources 58 may cease delivery of current during interval 66, e.g., for approximately 100-200 microseconds in some examples. Current sources 58 may then deliver second portion 64 of the biphasic waveform. Second portion 64 of the biphasic waveform may be referred to as "recharge waveform 64." FIG. 4B shows delivery of recharge waveform 64 by adjustable current sources 58. Adjustable current sources 58-2, 58-3 are illustrated as delivering recharge waveform 64. During delivery of recharge waveform 64, current sources 58-1, 58-4 are turned off (e.g., act as open circuits). During delivery of recharge waveform 64, voltage $V_C$ is monotonically decreased towards 0V, at which time a charge-balanced biphasic waveform has been delivered to the patient. The waveform $V_C$ illustrated in FIG. 5B may be repeated for each biphasic waveform delivered to the patient.

Figure 6:
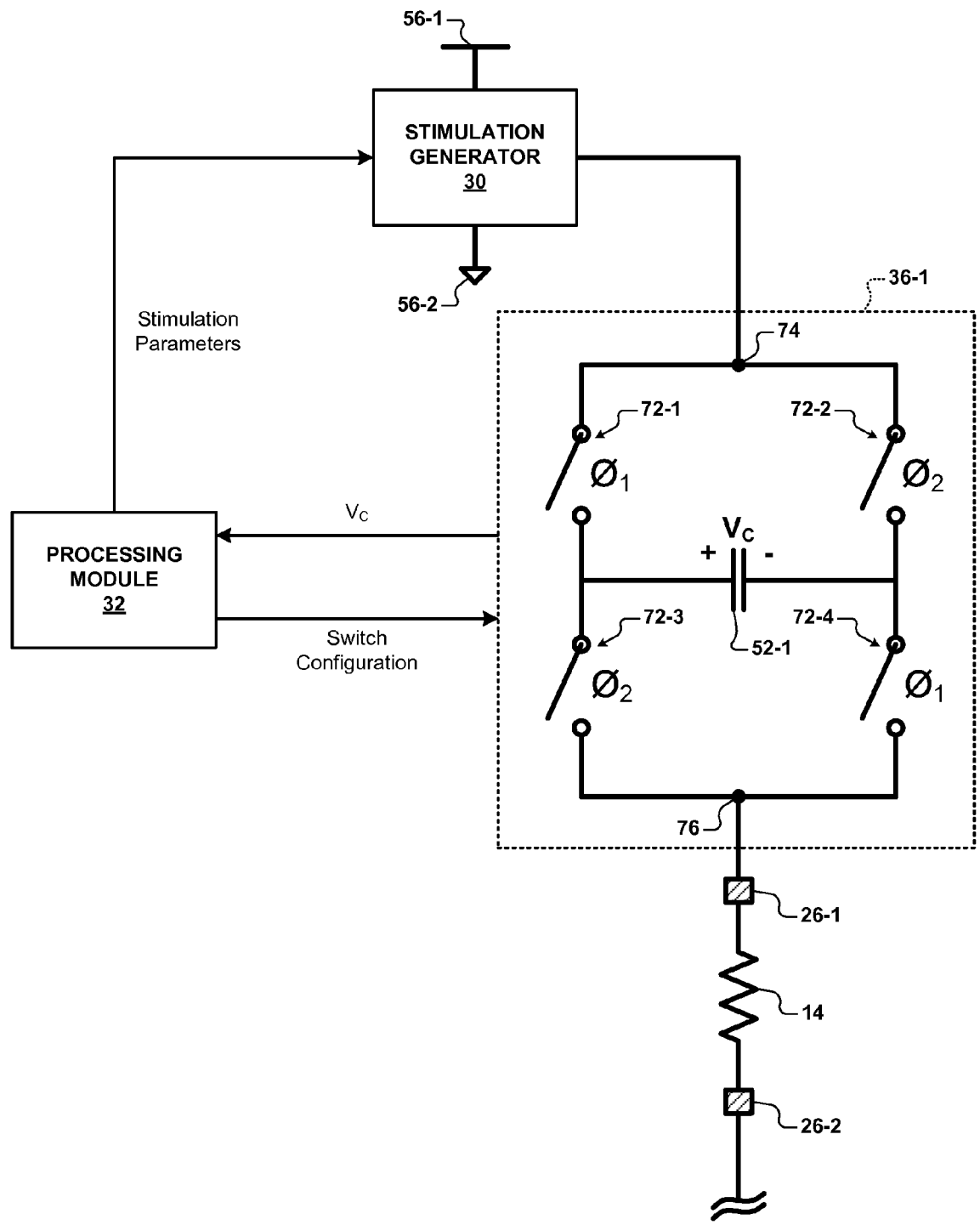
FIG. 6 shows an example coupling circuit of the present disclosure.

FIGS. 6-16 describe operation of example coupling circuits 36 that may maintain voltage across coupling capacitors 52 within a threshold voltage range while delivering a charge-balanced biphasic waveform. FIG. 6 shows an example coupling circuit 36-1. Coupling circuit 36-1 may operate in three different states. As described herein, coupling circuit 36-1 may operate in an open state, a first coupling state, and a second coupling state. Processing module 32 may control switches 72-1, 72-2, 72-3, 72-4 (collectively "switches 72") in order to control the state of coupling circuit 36-1. For example, processing module 32 may selectively open and close switches 72 in order to set the state of coupling circuit 36-1.

Figure 7:
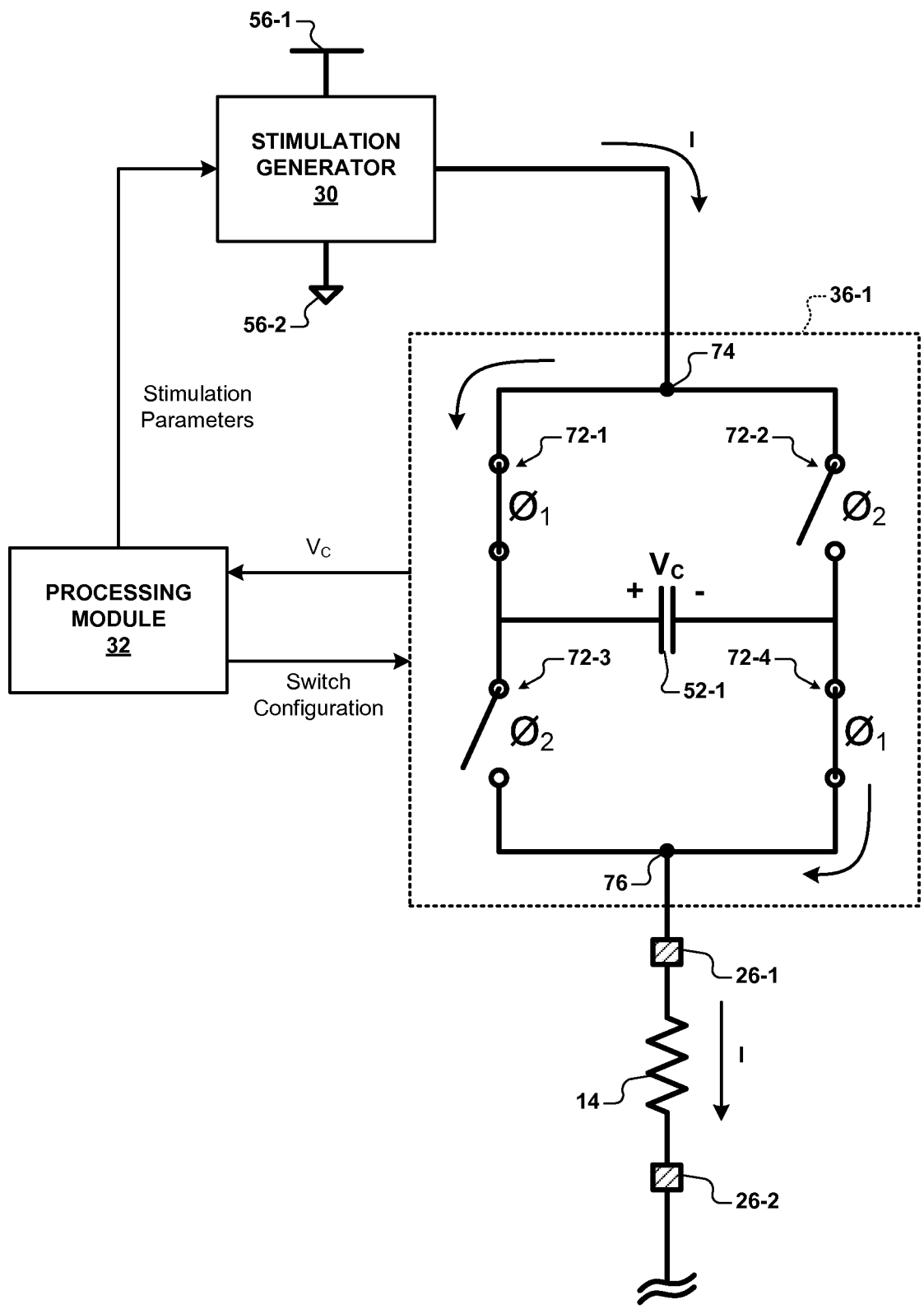
FIGS. 7 and 8 illustrate delivery of a current pulse to a patient via the coupling circuit of FIG. 6.
Figure 8:
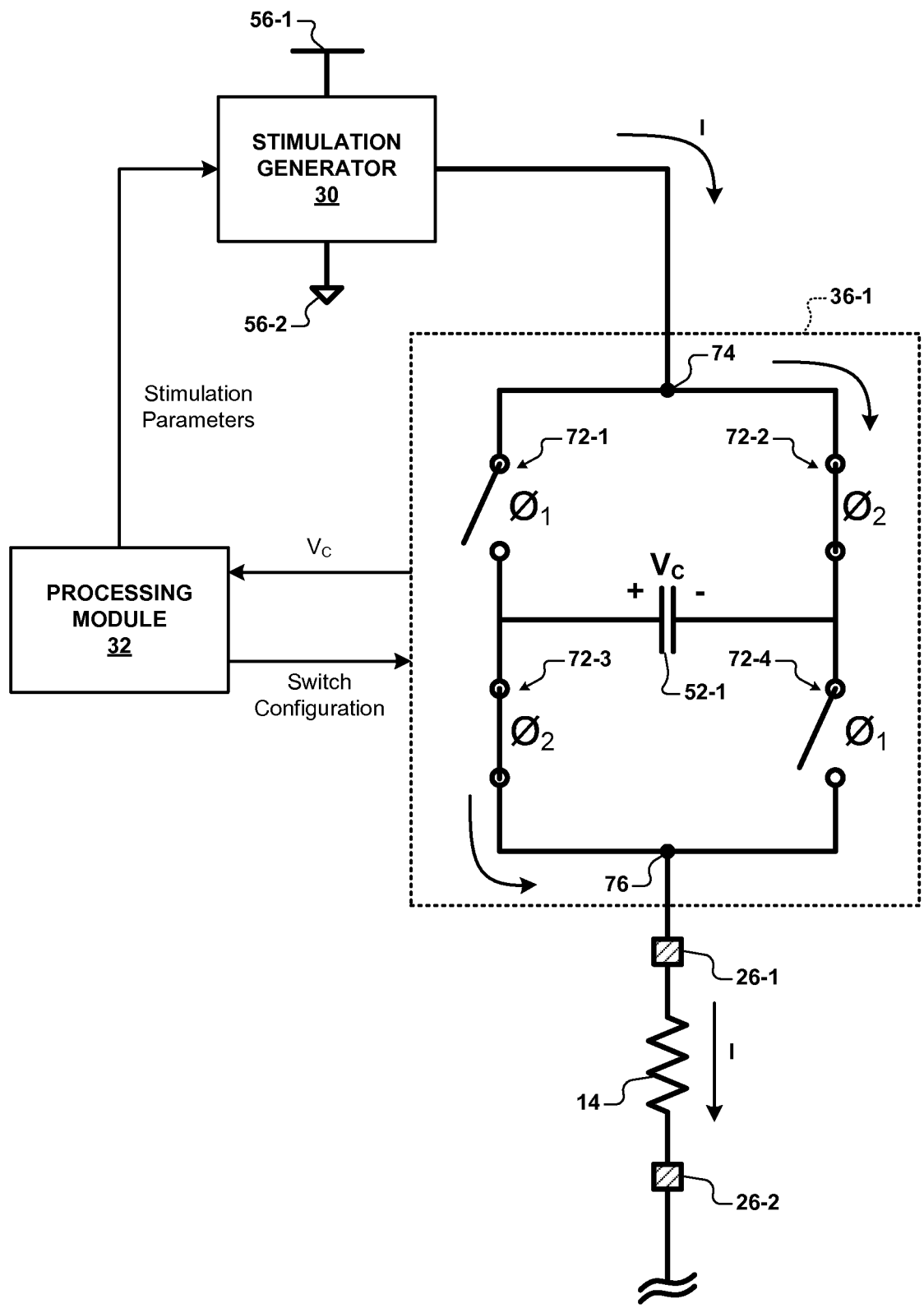

In an open state, as illustrated in FIG. 6, coupling circuit 36-1 may form an open circuit between electrode 26-1 and stimulation generator 30 (e.g., a stimulation engine shared by a plurality of electrodes or associated with only electrode 26-1). In other words, in the open state, coupling circuit 36-1 may disconnect stimulation generator 30 from electrode 26-1. In the first and second coupling states, coupling circuit 36-1 may capacitively couple stimulation generator 30 to electrode 26-1. In the first coupling state, coupling capacitor 52-1 is connected in a first orientation between stimulation generator 30 and electrode 26-1. In a second coupling state, coupling capacitor 52-1 is connected in a second orientation between stimulation generator 30 and electrode 26-1. Examples of the first coupling state and the second coupling state are illustrated in FIG. 7 and FIG. 8, respectively. Switches 72 are annotated using $\varnothing_1$ and $\varnothing_2$ symbols. Processing module 32 may close switches 72-1, 72-4, which are annotated using $\varnothing_1$ symbols, to set coupling circuit 36-1 to the first coupling state. Processing module 32 may close switches 72-2, 72-3, which are annotated using the $\varnothing_2$ symbols, to set coupling circuit 36-1 to the second coupling state.

Processing module 32 may control the states of switches 72 in order to set coupling circuit 36-1 in either the first coupling state or the second coupling state. As illustrated in FIG. 7, processing module 32 may close switches 72-1, 72-4 and open switches 72-2, 72-3 in order to place coupling circuit 36-1 in the first coupling state. As illustrated in FIG. 8, processing module 32 may close switches 72-2, 72-3 and open switches 72-1, 72-4 in order to place coupling circuit 36-1 in the second coupling state.

Coupling circuit 36-1 has a first node 74 that is connected to stimulation generator 30. Coupling circuit 36-1 has a second node 76 that is connected to electrode 26-1. Accordingly, processing module 32 may connect capacitor 52-1 between nodes 74, 76 in a first orientation to place coupling circuit 36-1 in the first coupling state. Alternatively, processing module 32 may connect capacitor 52-1 between nodes 74, 76 in a second orientation to place coupling circuit 36-1 in the second coupling state.

Figure 10:
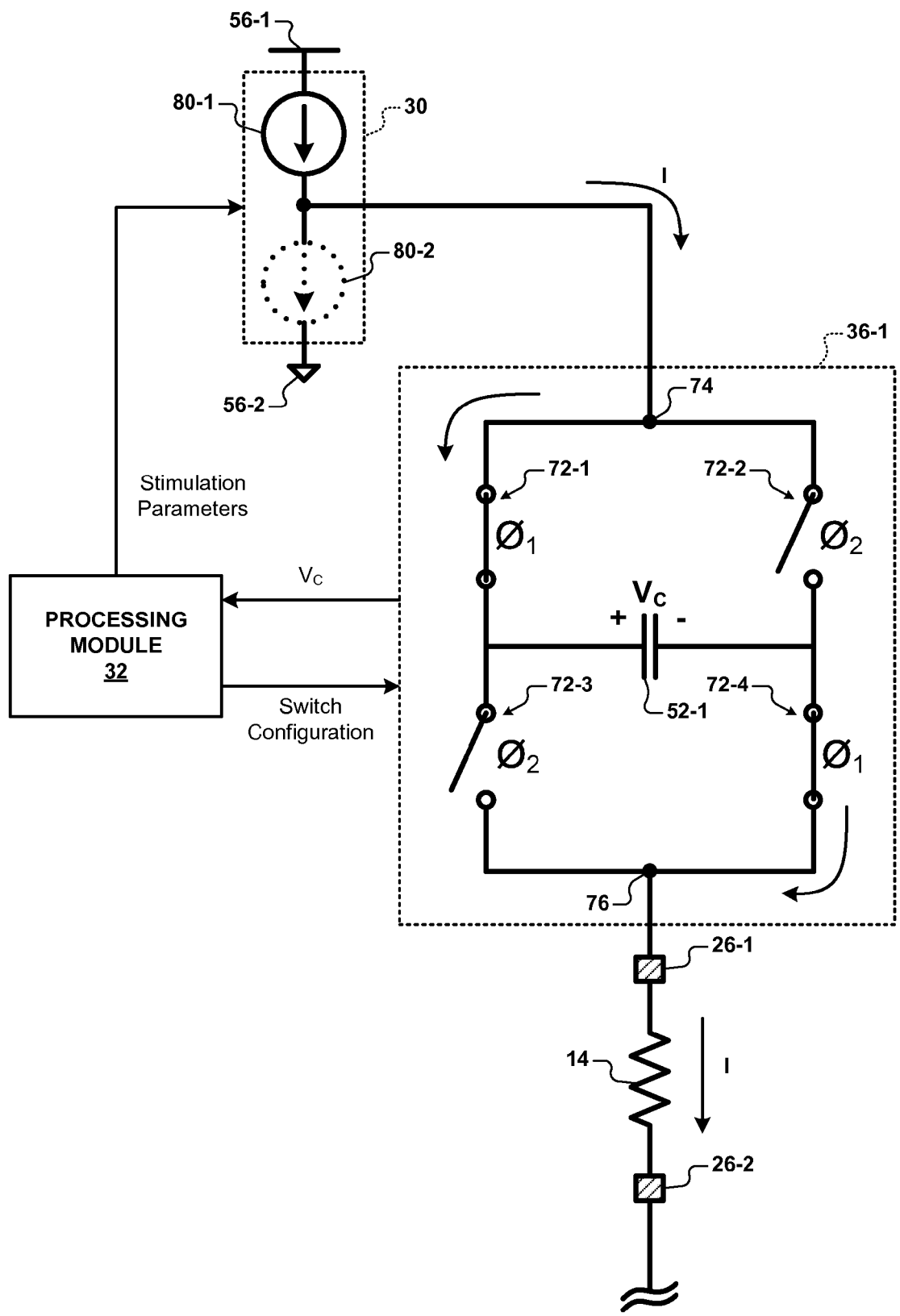
FIG. 10 illustrates an example stimulation generator that includes adjustable current sources.
Figure 11:
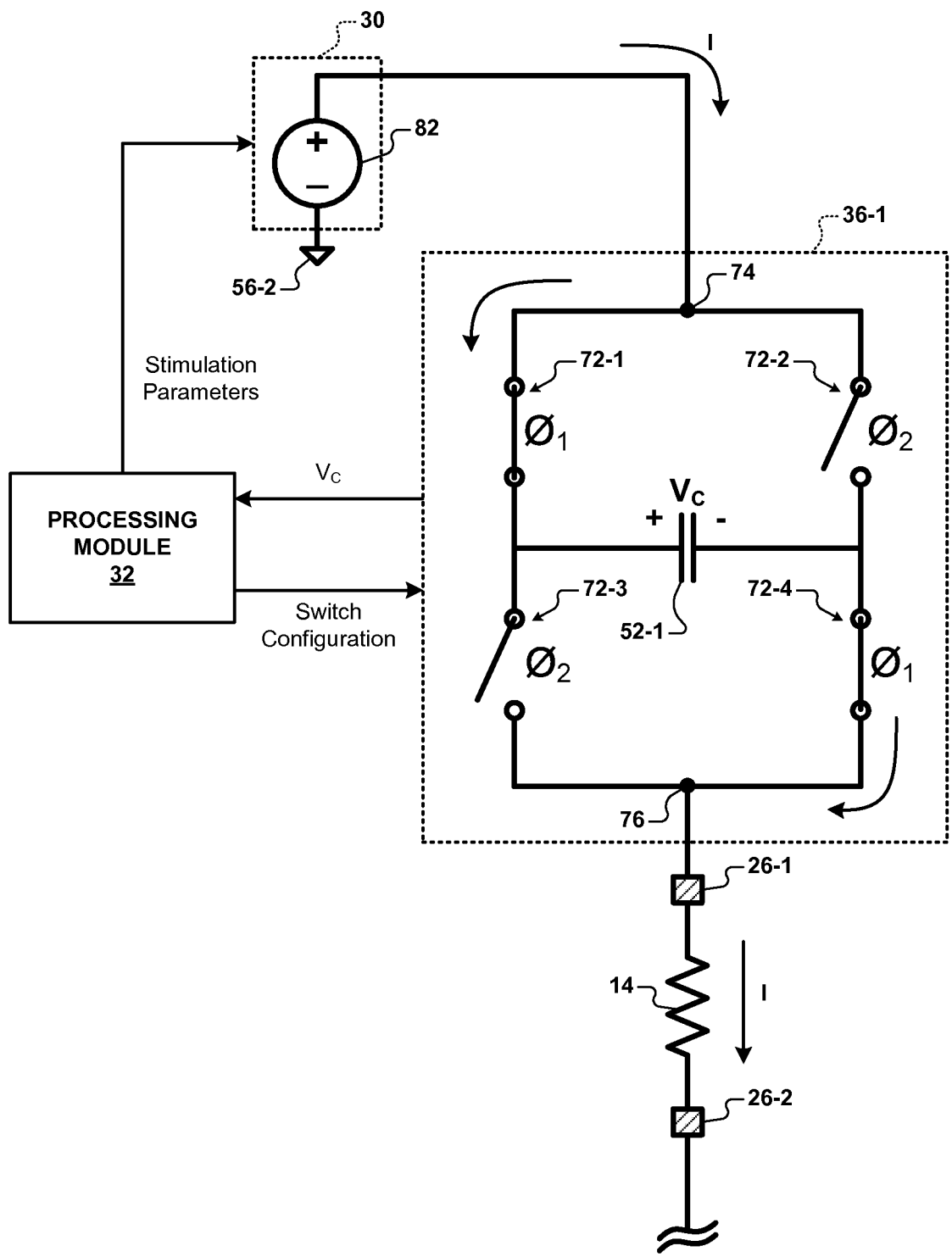
FIG. 11 illustrates an example stimulation generator that includes an adjustable voltage source.

In some examples, stimulation generator 30 may include an adjustable current source, e.g., as illustrated in FIG. 10. In examples where stimulation generator 30 includes an adjustable current source, processing module 32 may control the adjustable current source in order to control the magnitude and direction of the current delivered to patient 14 via electrode 26-1. In some examples, stimulation generator 30 may include an adjustable voltage source, e.g., as illustrated in FIG. 11. In examples where stimulation generator 30 includes an adjustable voltage source, processing module 32 may control the adjustable voltage source in order to control the magnitude and polarity of the voltage applied to patient 14 via electrode 26-1.

FIGS. 7-8 illustrate delivery of pulse 62 to patient 14 (i.e., patient tissue between electrodes 26-1 and 26-2) via electrode 26-1. Patient 14 is modeled as a resistor. Electrode 26-2, which receives current, is connected to a coupling circuit 36-2 (not shown in FIGS. 7-8) similar to coupling circuit 36-1 illustrated in FIGS. 7-8. Electrical stimulation delivered between both coupling circuits 36-1, 36-2 is illustrated in FIGS. 12A-13B, for example. Although electrical stimulation is illustrated and described herein with respect to coupling circuits 36-1, 36-2, and electrodes 26-1, 26-2, the techniques of the present disclosure may be applicable to stimulation between any combination of electrodes 26 and 28.

It may be assumed herein that initially, prior to delivery of a biphasic waveform to patient 14, coupling capacitor 52-1 has negligible stored charge. In other words, it may be assumed that prior to delivery of a biphasic waveform to patient 14, the voltage $V_C$ across coupling capacitor 52-1 may be 0V. Coupling capacitors 52 may be either unpolarized capacitors or polarized capacitors. Initially, operation of coupling circuit 36-1 is described herein using an unpolarized capacitor, e.g., with respect to FIGS. 6-16. Subsequently, operation of a coupling circuit is described using a polarized capacitor. Note that the voltage $V_C$ across coupling capacitor 52-1 includes polarity references (+) and (−). These polarity references aid the reader in understanding how coupling capacitor 52-1 is charged and discharged while stimulation generator 30 is generating electrical stimulation.

Figure 9:
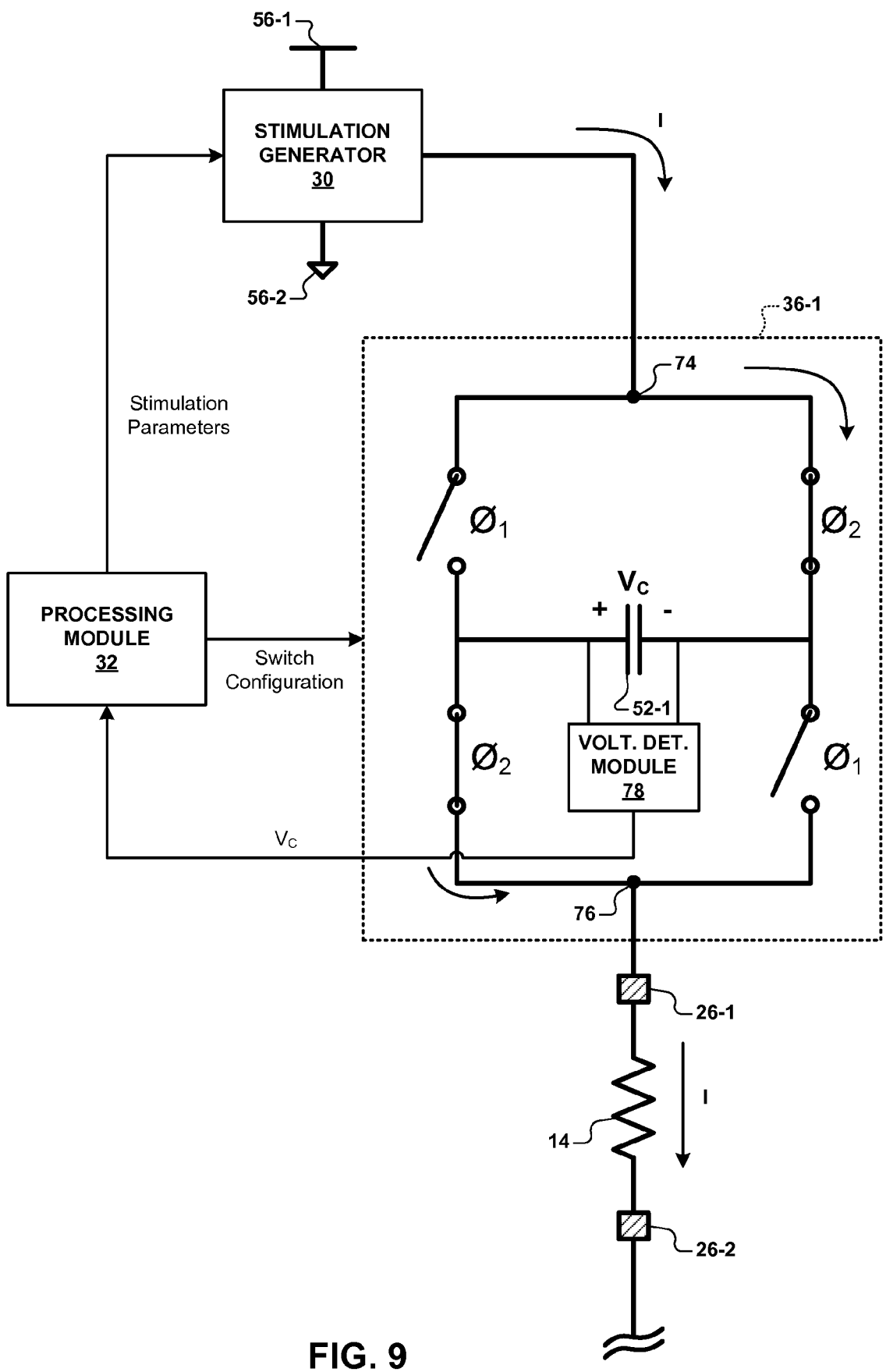
FIG. 9 shows a voltage detection module that may be used to determine the voltage across a coupling capacitor.

FIG. 9 shows an example voltage detection module 78 that may be used to determine the voltage across coupling capacitor 52-1. Although voltage detection module 78 is only illustrated in FIG. 9, it can be assumed that voltage detection module 78 is present in each of the coupling circuits described herein. Illustration of voltage detection module 78 is eliminated in other coupling circuits so that the reader may focus on other aspects of coupling circuit operation. Instead, in place of voltage detection module 78, an arrow is drawn from coupling circuits 36-1, 36-2 to processing module 32 to convey the information (e.g., $V_C$) transmitted to processing module 32 by voltage detection module 78.

Voltage detection module 78 may receive the voltage $V_C$ across coupling capacitor 52-1. Voltage detection module 78 may determine when the voltage $V_C$ across coupling capacitor 52-1 is equal to, or greater than a threshold magnitude $V_T$. Voltage detection module 78 indicates to processing module 32 when the voltage $V_C$ across coupling capacitor 52-1 is greater than the threshold magnitude $V_T$. For example, if the voltage $V_C$ increases from a value of 0V to $V_T$, voltage detection module 78 may indicate to processing module 32 when the voltage $V_C$ reaches $V_T$. Similarly, if the voltage $V_C$ increases from a value of 0V to a magnitude of $-V_T$, voltage detection module 78 may indicate to processing module 32 when the voltage $V_C$ reaches $-V_T$. In other words, processing module 32 may determine when the voltage across coupling capacitor 52-1 has reached a magnitude of $V_T$ based on the output of voltage detection module 78.

In some examples, voltage detection module 78 may include one or more comparator circuits configured to indicate when the magnitude of the voltage $V_C$ has reached a threshold voltage $V_T$. For example, voltage detection module 78 may include a comparator circuit that compares voltage $V_C$ to a positive threshold voltage $V_T$ and outputs a signal (e.g., a digital value) to processing module 32 indicating whether $V_C$ is greater than $V_T$. Additionally, voltage detection module 78 may include a comparator circuit that compares voltage $V_C$ to a negative threshold voltage $-V_T$ and outputs a signal (e.g., a digital value) to processing module 32 indicating whether $V_C$ is greater than (e.g., more negative than) $-V_T$.

As described hereinafter, voltage detection module 78 may also output a signal to processing module 32 to indicate when the voltage $V_C$ has reached 0V. Such an output signal may allow processing module 32 to determine when coupling capacitor 52-1 has been completely discharged. Such functionality may allow processing module 32 to determine when to discontinue recharge waveform 64. In some examples, voltage detection module 78 may determine the voltage $V_C$ across coupling capacitor 52-1 using other circuits, such as an analog-to-digital converter circuit.

The range of voltages between $V_T$ and $-V_T$ may be referred to herein as a "threshold voltage range." Although the threshold voltages that define the threshold voltage range are described herein as having equal magnitude (e.g., $V_T$ and $-V_T$), in some examples, the positive threshold voltage and the negative threshold voltage may have different magnitudes. For example, when coupling capacitors 52 are polarized capacitors, the threshold voltage range may range from 0V up to $V_T$, or from 0V to $-V_T$. Regardless of the magnitudes and polarities of the threshold voltages, the range of voltages between such threshold voltages may be referred to as a "threshold voltage range."

Processing module 32 may perform two general functions while controlling stimulation generator 30 to deliver the biphasic waveform. First, processing module 32 may control coupling circuit 36-1 to maintain the voltage $V_C$ within the threshold voltage range. To accomplish this, processing module 32 may switch the orientation of coupling capacitor 52-1 within coupling circuit 36-1 during delivery of the biphasic waveform, which may cause coupling capacitor 52-1 to be charged and discharged a number of times during delivery of the biphasic waveform. Second, processing module 32 may store a value indicating the number of times the orientation of coupling capacitor 52-1 was switched during delivery of pulse 62 so that processing module 32 may determine a number of times capacitor orientation should be switched during recharge waveform 64 in order to achieve a charge-balanced biphasic waveform.

Processing module 32 may control the state of coupling circuit 36-1 in order to maintain the voltage $V_C$ within the threshold voltage range (e.g., between $-V_T$ and $V_T$) during delivery of the biphasic waveform. Switching the state of coupling circuit 36-1 in order to maintain the voltage $V_C$ within the threshold voltage range during delivery of pulse 62 of a biphasic waveform is now described with respect to FIGS. 6-8. Subsequently, delivery of a complete biphasic waveform is described with respect to FIGS. 12A-14, for example.

It may be assumed that coupling capacitor 52-1 is discharged and $V_C$ is at 0V prior to delivery of pulse 62. Such a scenario may be represented by FIG. 6 in which coupling circuit 36-1 is in an open state. Processing module 32 may begin delivery of the biphasic waveform, e.g., begin delivery of pulse 62, by closing switches 72-1, 72-4 of coupling circuit 36-1, as illustrated in FIG. 7. Processing module 32 may then control stimulation generator 30 to deliver pulse 62 of the biphasic waveform. In examples where stimulation generator 30 includes an adjustable current source, processing module 32 may control the magnitude and direction of current generated by the adjustable current source. In examples where stimulation generator 30 includes an adjustable voltage source, processing module 32 may control the magnitude and polarity of the voltage generated by the adjustable voltage source.

With respect to FIG. 7, the arrows indicate direction of current generated by stimulation generator 30 and delivered to patient 14. The direction of current generated in FIG. 7 may be referred to herein as a first direction of current, which may be in a direction that is opposite to a second direction of current delivered during recharge waveform 64. In the first coupling state of FIG. 7, coupling capacitor 52-1 is connected between nodes 74, 76 in a first orientation while stimulation generator 30 delivers current in the first direction. Coupling capacitor 52-1 charges during delivery of pulse 62. For example, coupling capacitor 52-1 may charge such that the voltage $V_C$ is positive. Charging of coupling capacitor 52-1 during the first coupling state towards a more positive value of $V_C$ may be referred to as charging coupling capacitor 52-1 to a first voltage polarity.

At some point during delivery of pulse 62, the voltage $V_C$ may reach the positive threshold voltage $V_T$. For example, during delivery of the pulse, the voltage $V_C$ may monotonically increase to a more positive value until $V_C$ is equal to the positive threshold voltage $V_T$. Voltage detection module 78 may determine when voltage $V_C$ reaches the positive threshold voltage $V_T$. Voltage detection module 78 may indicate to processing module 32 when the voltage $V_C$ reaches the positive threshold voltage $V_T$, or at least provide an output based on which processing module 32 determines when the voltage $V_C$ reaches the positive threshold voltage $V_T$.

Processing module 32 may transition coupling circuit 36-1 from the first coupling state to the second coupling state when voltage detection module 78 indicates that the voltage $V_C$ has reached the positive threshold voltage $V_T$. For example, processing module 32 may transition coupling circuit 36-1 from the first coupling state to the second coupling state in response to determining that the output generated by voltage detection module 78 indicates that the voltage $V_C$ has reached the positive threshold voltage $V_T$. FIG. 8 illustrates the second coupling state of coupling circuit 36-1 during delivery of pulse 62. In order to transition coupling circuit 36-1 from the first coupling state to the second coupling state, processing module 32 may close switches 72-2, 72-3 and open switches 72-1, 72-4. In some examples, processing module 32 may implement a break-before-make transition in which processing module 32 controls switches 72-1, 72-4 to open slightly before instructing switches 72-2, 72-4 to close.

With respect to FIG. 8, the voltage $V_C$ across coupling capacitor 52-1 is initially at the same value ($V_T$) as it was just prior to the transition to the second coupling state. Additionally, the direction of stimulation during delivery of pulse 62 is in the same direction as it was just prior to the transition to the second coupling state. However, since coupling capacitor 52-1 has transitioned from the first orientation to the second orientation, the current generated by stimulation generator 30 may tend to discharge coupling capacitor 52-1 towards a value of 0V. Eventually, the current generated by stimulation generator 30 may charge coupling capacitor 52-1 to a negative voltage. For example, the current generated by stimulation generator 30 may charge coupling capacitor 52-1 to the negative threshold voltage $-V_T$ (i.e., a voltage having a second polarity).

Accordingly, at some point during delivery of pulse 62, the voltage $V_C$ may reach the negative threshold $-V_T$. Voltage detection module 78 may determine when voltage $V_C$ reaches the negative threshold voltage $-V_T$. Voltage detection module 78 may indicate to processing module 32 when the voltage $V_C$ reaches the negative threshold voltage $-V_T$, or at least provide an output based on which processing module 32 determines when the voltage $V_C$ reaches the negative threshold voltage $-V_T$.

Processing module 32 may transition coupling circuit 36-1 from the second coupling state to the first coupling state when voltage detection module 78 indicates that the voltage $V_C$ has reached the negative threshold voltage $-V_T$. For example, processing module 32 may transition coupling circuit 36-1 from the first coupling state to the second coupling state in response to determining that the output generated by voltage detection module 78 indicates that the voltage $V_C$ has reached the negative threshold voltage $-V_T$. As described above, FIG. 7 illustrates the first coupling state of coupling circuit 36-1. In order to transition coupling circuit from the second coupling state to the first coupling state, processing module 32 may close switches 72-1, 72-4 and open switches 72-2, 72-3. In some examples, processing module 32 may implement a break-before-make transition in which processing module 32 controls switches 72-2, 72-3 to open slightly before instructing switches 72-1, 72-2 to close.

With respect to FIG. 7, the voltage $V_C$ across coupling capacitor 52-1 is initially at the same value ($-V_T$) it was just prior to the transition back to the first coupling state. Additionally, the direction of stimulation during delivery of pulse 62 is in the same direction as it was just prior to the transition back to the first coupling state. However, since coupling capacitor 52-1 has transitioned from the second orientation to the first orientation, the current generated by stimulation generator 30 may tend to discharge coupling capacitor 52-1 from $-V_T$ towards a value of 0V. Eventually, the current generated by stimulation generator 30 may charge coupling capacitor 52-1 to a positive voltage. For example, the current generated by stimulation generator 30 may charge coupling capacitor 52-1 to the positive threshold voltage $V_T$.

As described above, processing module 32 may control stimulation generator 30 to deliver electrical stimulation while at the same time monitoring the voltage across coupling capacitor 52-1. In the event that the voltage $V_C$ reaches a threshold magnitude (e.g., $V_T$ or $-V_T$), processing module 32 may transition the state of coupling circuit 36-1. In this manner, processing module 32 may control the coupling state of coupling circuit 36-1 to maintain the voltage $V_C$ within a threshold voltage range.

It should be noted that, in some examples, processing module 32 may independently control the output of stimulation generator 30 and the state of coupling circuit 36-1. For example, processing module 32 may control stimulation generator 30 to generate stimulation according to parameters (illustrated as "stimulation parameters" in FIGS. 6-13B) stored in memory 34 without regard to the voltage $V_C$ across coupling capacitor 52-1. Processing module 32 may transition the state of coupling circuit 36-1 from one state to another state based on when the voltage $V_C$ reaches a threshold magnitude, regardless of the output of stimulation generator 30.

Put another way, processing module 32 controls the state of coupling circuit 36-1 based on the voltage $V_C$ and controls stimulation generator 30 based on the programmed stimulation parameters.

Since processing module 32 may independently control the output of stimulation generator 30 and the state of coupling circuit 36-1, the coupling circuit of the present disclosure may be implemented in electrical stimulation devices (e.g., IMD 16) without modification of the circuitry that generates stimulation (e.g., stimulation generator 30). In other words, the coupling circuit of the present disclosure may be implemented within currently existing electrical stimulation devices with minimal if any modification to the currently existing electrical stimulation electronics.

As described above, stimulation generator 30 may include an adjustable voltage source and/or adjustable current source that generates electrical stimulation. FIG. 10 illustrates an example stimulation generator 30 that includes adjustable current sources 80-1, 80-2. Processing module 32 may adjust both the magnitude and direction of current delivered by adjustable current sources 80-1, 80-2. In FIG. 10, processing module 32 may control current source 80-1 to deliver stimulation in the direction illustrated. Current source 80-2 may be turned off in FIG. 10. In other words, current source 80-2, illustrated by dotted lines, may act as an open circuit. In examples where processing module 32 controls adjustable current sources 80-1, 80-2 to deliver recharge waveform 64, processing module 32 may turn on current source 80-2 and turn off current source 80-1.

FIG. 11 illustrates an example stimulation generator 30 that includes an adjustable voltage source 82. Processing module 32 may adjust both the magnitude and polarity of the voltage delivered by adjustable voltage source 82. In FIG. 11, processing module 32 may control adjustable voltage source 82 to deliver a positive voltage to generate current in the direction illustrated. Processing module 32 may also control adjustable voltage source 82 to deliver a voltage having a negative polarity in order to reverse the direction of current delivered to patient, e.g., during recharge waveform 64.

Figure 12A:
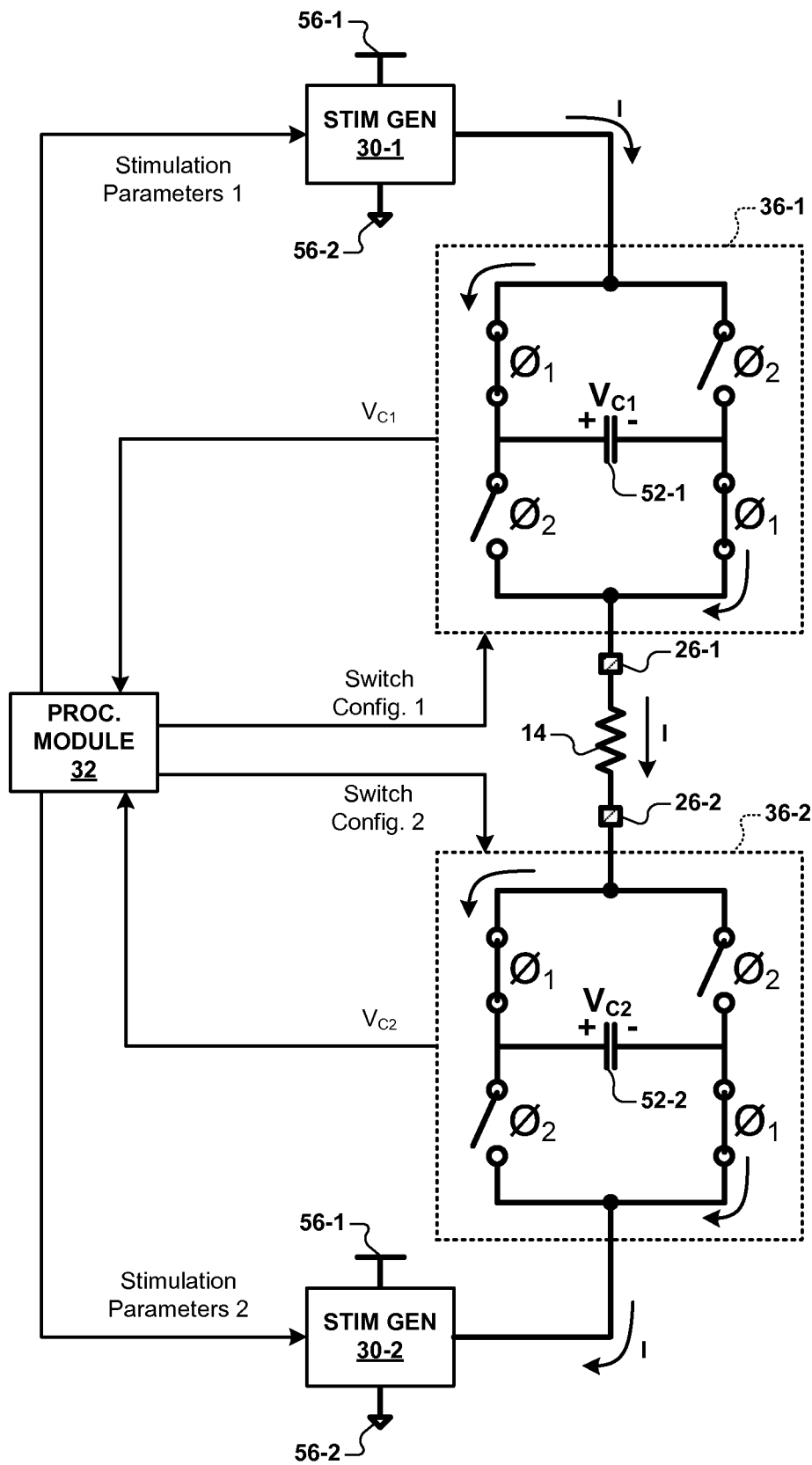
FIG. 12A illustrates coupling circuits in a first coupling state during delivery of a current pulse.
Figure 12B:
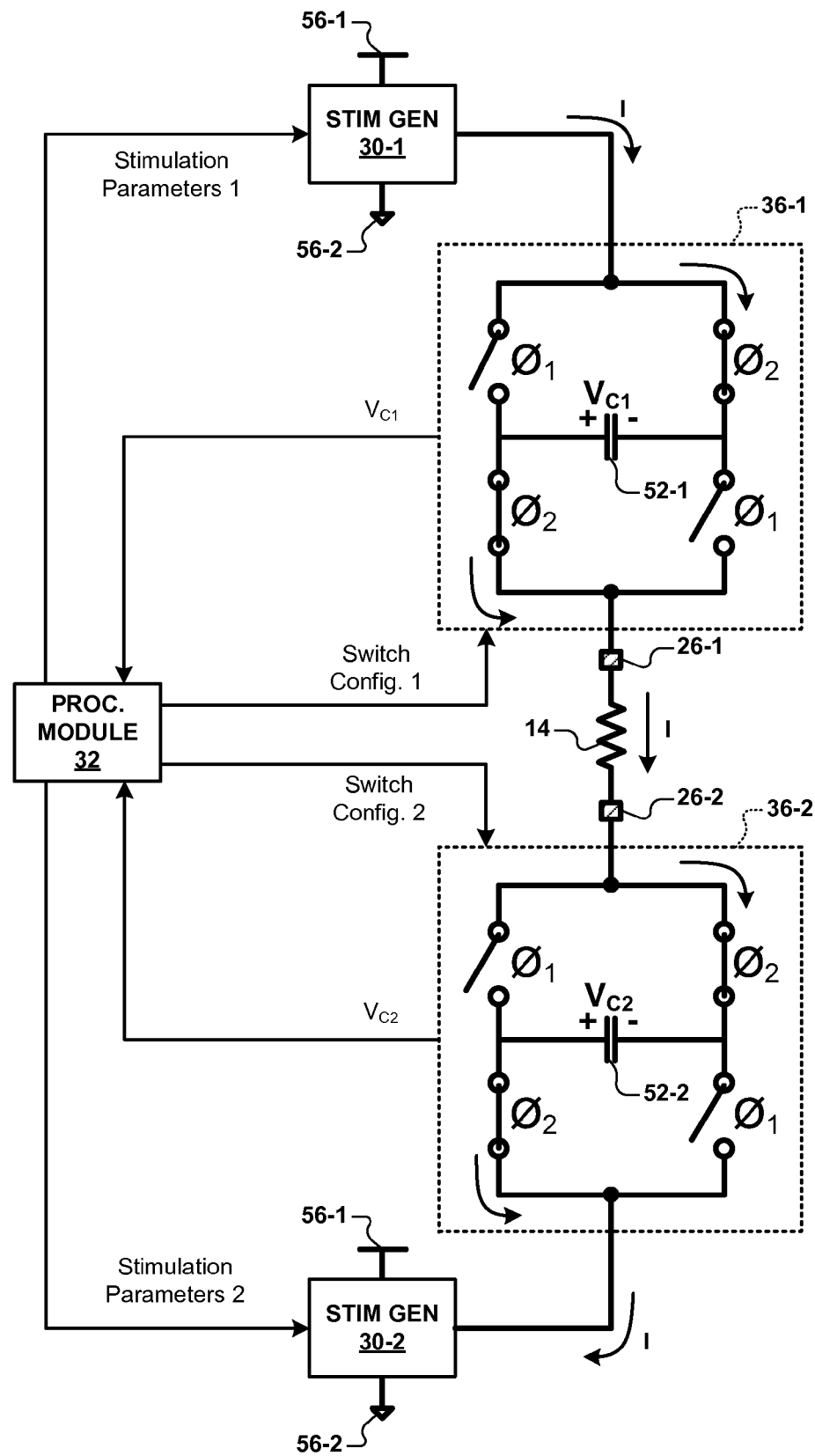
FIG. 12B illustrates coupling circuits in a second coupling state during delivery of a current pulse.
Figure 13A:
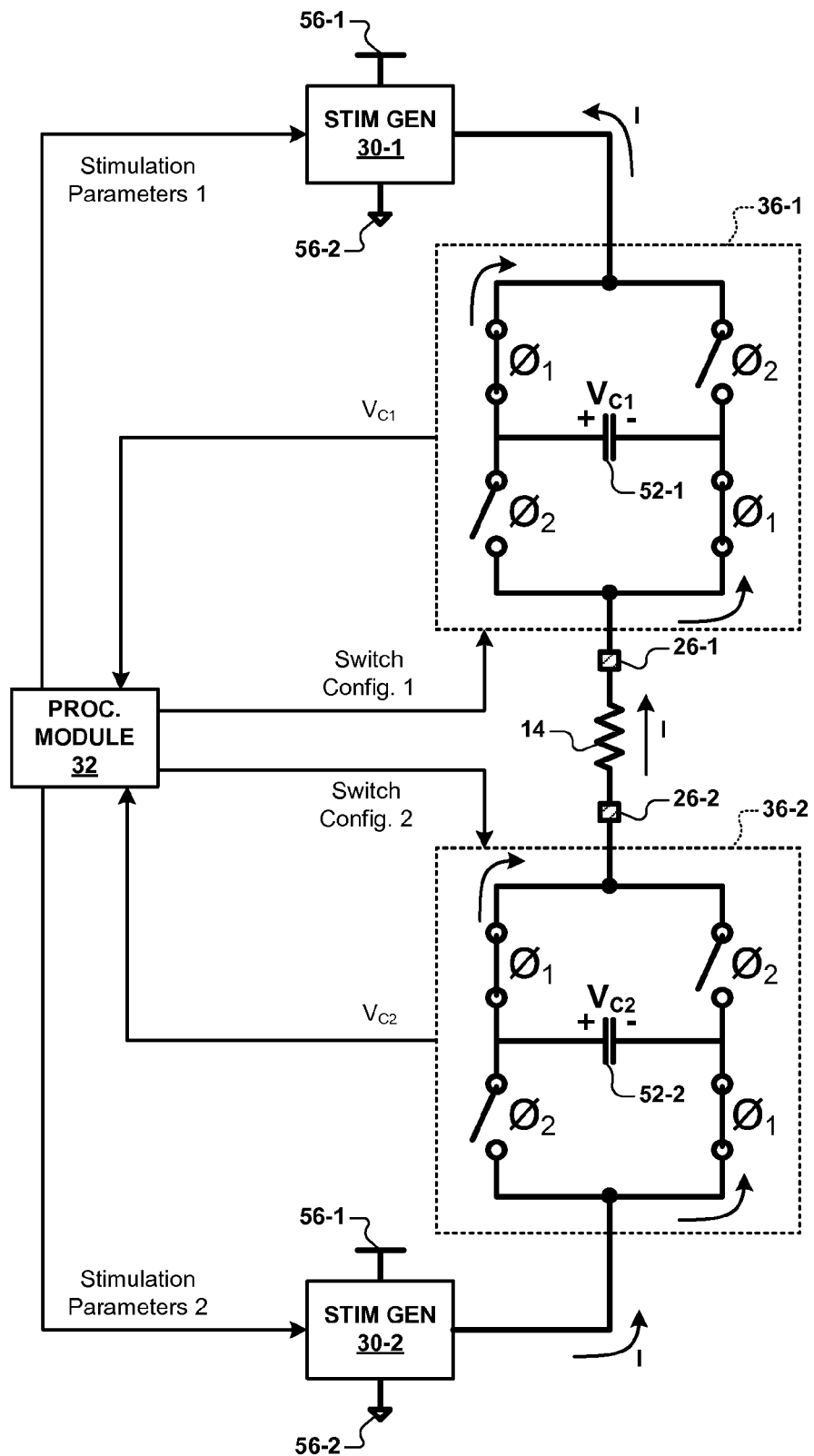
FIG. 13A illustrates coupling circuits in the first coupling state during delivery of a recharge waveform.
Figure 13B:
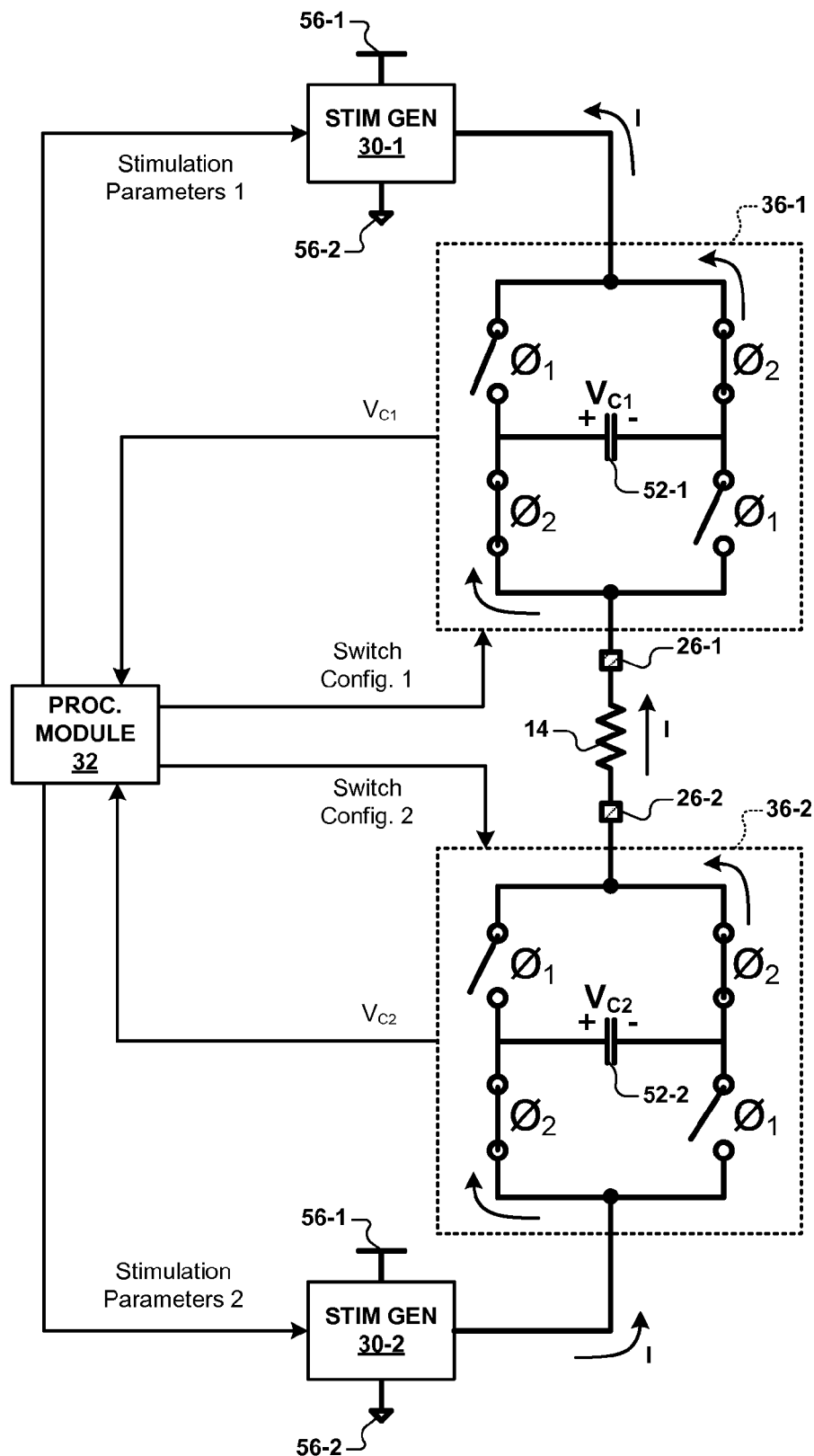
FIG. 13B illustrates coupling circuits in the second coupling state during delivery of a recharge waveform.

FIGS. 12A-13B show delivery of a biphasic waveform using two electrodes 26-1, 26-2. FIGS. 12A-12B illustrate delivery of pulse 62 of the biphasic waveform. FIG. 12A illustrates coupling circuits 36-1, 36-2 in the first coupling state during delivery of pulse 62. FIG. 12B illustrates coupling circuits 36-1, 36-2 in the second coupling state during delivery of pulse 62. FIG. 13A illustrates coupling circuits 36-1, 36-2 in the first coupling state during delivery of recharge waveform 64. FIG. 13B illustrates coupling circuits 36-1, 36-2 in the second coupling state during delivery of recharge waveform 64. FIG. 14 shows the voltage $V_{C1}$ across coupling capacitor 52-1 during delivery of pulse 62 and recharge waveform 64.

Delivery of a biphasic waveform is now described with respect to FIGS. 12A-14. FIG. 12A shows delivery of pulse 62 of the biphasic waveform. Initially, it may be assumed that the voltages $V_{C1}$ and $V_{C2}$ across coupling capacitors 52-1, 52-2 are equal to 0V. In FIG. 12A, processing module 32 controls coupling circuits 36-1, 36-2 to operate in the first coupling state. Processing module 32 then controls stimulation generators 30-1, 30-2 to deliver pulse 62.

Stimulation generators 30-1, 30-2 are components of stimulation generator 30 and may each be, for example, a stimulation engine. For example, stimulation generator 30-1 may represent circuitry that delivers stimulation associated with coupling circuit 36-1 and electrode 26-1. Similarly, stimulation generator 30-2 may represent circuitry that delivers stimulation associated with coupling circuit 36-2 and electrode 26-2. In some examples, stimulation generators 30-1, 30-2 may represent circuitry that is dedicated to delivering stimulation via the associated coupling circuits 36-1, 36-2, respectively, and electrodes 26-1, 26-2, respectively.

Although delivery of a biphasic stimulation waveform between two electrodes 26-1, 26-2 is illustrated and described herein, coupling circuits 36 of the present disclosure may be used during delivery of stimulation between any combination of electrodes. For example, coupling circuits 36 may be used when stimulation is sourced from one electrode and sunk via two electrodes, sourced from two electrodes and sunk via one electrode, etc.

Processing module 32 may instruct stimulation generators 30-1, 30-2 to deliver electrical stimulation that is equal in magnitude, but opposite in direction. For example, when stimulation generators 30-1, 30-2 include adjustable current sources, processing module 30-1, 30-2 may instruct the adjustable current sources to deliver current having equal magnitude but opposite directions. With respect to FIGS. 12A-12B, stimulation generator 30-1 is configured to source an amount of current while stimulation generator 30-2 is configured to sink an equal amount of current.

Processing module 32 may control the coupling state of coupling circuit 36-1 based on the voltage $V_{C1}$ developed across coupling capacitor 52-1. Processing module 32 may control the coupling state of coupling circuit 36-2 based on the voltage $V_{C2}$ developed across coupling capacitor 52-2. Coupling capacitors 52-1, 52-2 may tend to develop voltages at different rates, which may result in $V_{C1}$ having a different value than $V_{C2}$. Although coupling capacitors 52-1, 52-2 may tend to develop voltages at different rates, in some examples, coupling capacitors 52-1, 52-2 may develop voltages at nearly the same rate, which may result in $V_{C1}$ having a value that is nearly equal to $V_{C2}$. Since processing module 32 may independently control the coupling states of coupling circuits 36-1, 36-2 based on the respective voltages $V_{C1}$ and $V_{C2}$, processing module 32 may set the coupling states of coupling circuits 36-1, 36-2 to different coupling states in examples where $V_{C1}$ and $V_{C2}$ have different values. For example, if $V_{C1}$ reaches the positive voltage threshold $V_T$ prior to $V_{C2}$ reaching the positive threshold voltage $V_T$, processing module 32 may switch the coupling state of coupling circuit 36-1 to the second coupling state while maintaining the coupling state of coupling circuit 36-2 in the first coupling state. Subsequently, when voltage $V_{C2}$ reaches $V_T$, processing module 32 may set the coupling circuit 36-2 to the second coupling state.

At the start of pulse 62, coupling capacitors 52-1, 52-2 are charged to a positive voltage. Processing module 32 monitors the voltages $V_{C1}$ and $V_{C2}$ to determine when the voltages $V_{C1}$ and $V_{C2}$ reach the positive threshold voltage $V_T$. Coupling capacitors 52-1, 52-2 may tend to develop voltages at slightly different rates. Accordingly, although first and second coupling circuits 36-1, 36-2 are illustrated as being in the same coupling states in FIGS. 12A-13B, since processing module 32 may control the states of coupling circuits 36-1, 36-2 independently, processing module 32 may switch the coupling states of coupling circuits 36-1, 36-2 independently of one another.

Processing module 32 may independently transition coupling circuits 36-1, 36-2 from the first coupling state to the second coupling state depending on when the voltages $V_{C1}$ and $V_{C2}$ reach the positive threshold voltage $V_T$. The voltage waveform $V_{C1}$ with respect to time is illustrated in FIG. 14. Although not illustrated, it may be assumed that a similar waveform exists for voltage $V_{C2}$. The coupling state of coupling circuit 36-1 is indicated under the voltage waveform for $V_{C1}$.

The number of transitions between coupling states for coupling circuit 36-1 is indicated under the coupling state in FIG. 14. The transition from the first coupling state to the second coupling state is the first transition. In some examples, processing module 32 may maintain a count of the number of transitions of coupling circuit 36-1 during delivery of pulse 62 in order to assure that a charge-balanced waveform is delivered, as described hereinafter. Transition counter 84, stored in memory 34, may store the count. The count may be an indicator of the amount of stimulation delivered to patient 14. The voltage across coupling capacitor 52-1 at any instant in time may not indicate the total amount of charge transferred to patient 14 because coupling capacitor 52-1 may be charged and discharged repeatedly during delivery of pulse 62. Transition counter 84 may be maintained by processing module 32 so that processing module 32 may determine when a charge-balanced waveform has been delivered during recharge waveform 64. Although the transition count illustrated in FIG. 14 is for coupling circuit 52-1, processing module 32 may also store a transition count for coupling circuit 52-2 and additional coupling circuits of IMD 16.

FIG. 12B shows delivery of pulse 62 when coupling circuits 36-1, 36-2 are in the second coupling state. The voltages $V_{C1}$ and $V_{C2}$ across coupling capacitors 52-1, 52-2 may begin to decrease towards 0V upon transitioning to the second coupling state. Note that the direction of current delivered to patient 14 does not change as a result of transitioning between coupling states. Instead, the direction of current delivered to patient 14 is maintained in the same direction in the first and second coupling states. However, since the orientations of coupling capacitors 52-1, 52-2 have been inverted within coupling circuits 36-1, 36-2, coupling capacitors 52-1, 52-2 are discharged upon transitioning from the first coupling state to the second coupling state.

Charging of coupling capacitor 52-1 to $-V_T$ is illustrated in the waveform of FIG. 14. Coupling capacitor 52-2 may charge to $-V_T$ in a similar manner. The duration of the second coupling state is illustrated under the waveform. Processing module 32 may determine when the voltages $V_{C1}$ and $V_{C2}$ have reached the negative threshold voltage $-V_T$ and transition coupling circuits 36-1, 36-2 from the second coupling state to the first coupling state when $V_{C1}$ and $V_{C2}$ reach the negative threshold voltage $-V_T$ (e.g., in response to determining that $V_{C1}$ and $V_{C2}$ have reached the negative threshold voltage $-V_T$). Processing module 32 may increment the transition count number (e.g., to 2 in this case) for each of coupling circuits 36-1, 36-2 based on the number of transitions that have occurred during delivery of pulse 62.

Referring back to FIG. 12A, electrical stimulation may charge coupling capacitors 52-1, 52-2 to $V_T$ when coupling circuits 36-1, 36-2 are in the first coupling state. Processing module 32 may transition coupling circuits 36-1, 36-2 from the first coupling state to the second coupling state when voltage detection module 78 indicates that voltages $V_{C1}$ and $V_{C2}$ have reached the positive threshold voltage $V_T$ (e.g., in response to determining that $V_{C1}$ and $V_{C2}$ have reached the positive threshold voltage $V_T$). Processing module 32 may then increment the transition counters (e.g. to 3) upon transitioning coupling circuits 36-1, 36-2 from the first coupling state to the second coupling state.

Referring now to FIG. 14, during delivery of pulse 62 in the second coupling state, with transition count equal to 3, processing module 32 terminates pulse 62 according to programmed parameters. The termination of pulse 62 occurs prior to the voltages $V_{C1}$ and $V_{C2}$ reaching the negative threshold voltage $-V_T$. At the end of pulse 62, processing module 32 may cease stimulation for an interval of time, indicated at 66. During interval 66, processing module 32 may set the state of coupling circuits 36-1, 36-2 to the open state in some examples. The voltages $V_{C1}$ and $V_{C2}$ across coupling capacitors 52-1, 52-2 may be maintained at a constant voltage in the open circuit state.

After interval 66, processing module 32 may control coupling circuits 36-1, 36-2 during delivery of recharge waveform 64. In order to start recharge waveform 64 after interval 66, processing module 32 may set coupling circuits 36-1, 36-2 to the same coupling state at the end of pulse 62 (e.g., the second coupling state in FIG. 14). In examples where the interval is eliminated, processing module 32 may maintain the same coupling states during the transition from delivering pulse 62 to delivering recharge waveform 64.

After setting the coupling states of coupling circuits 36-1, 36-2, processing module 32 may instruct stimulation generators 30-1, 30-2 to deliver recharge waveform 64. Recharge waveform 64 may have a polarity that is opposite to that of pulse 62. Delivery of recharge waveform 64 is illustrated in FIGS. 13A-13B. As illustrated, current is delivered to patient 14 in a second direction that is opposite to that delivered during delivery of pulse 62.

Initially, processing module 32 sets coupling circuits 36-1, 36-2 to the second coupling state while instructing stimulation generators 30-1, 30-2 to deliver recharge waveform 64. During delivery of recharge waveform 64, the voltages $V_{C1}$ and $V_{C2}$ may trend towards the positive threshold voltage $V_T$. Processing module 32 may determine when the voltages $V_{C1}$ and $V_{C2}$ reach the positive threshold voltage $V_T$ based on indications from voltage detection module 78.

Processing module 32 may transition coupling circuits 36-1, 36-2 from the second coupling state to the first coupling state during delivery of recharge waveform 64 when voltage detection module 78 indicates that voltages $V_{C1}$ and $V_{C2}$ have reached the positive threshold voltage $V_T$. Additionally, processing module 32 may decrement the transition counters after transitioning coupling circuits 36-1, 36-2 (e.g., from 3 to 2 in this case).

Processing module 32 may continue instructing stimulation generators 30-1, 30-2 to deliver recharge waveform 64 until $V_{C1}$ and $V_{C2}$ reach the negative threshold voltage $-V_T$. Upon reaching $-V_T$, processing module 32 may transition coupling circuits 36-1, 36-2 from the first coupling state to the second coupling state. Additionally, processing module 32 may decrement the transition counters (e.g., from 2 to 1) when transitioning from the first coupling state to the second coupling state. After $V_{C1}$ and $V_{C2}$ reach the positive threshold voltage $V_T$ in the second coupling state, processing module 32 may transition coupling circuits 36-1, 36-2 a final time from the second coupling state to the first coupling state.

Upon transitioning coupling circuits 36-1, 36-2 to the first coupling state, processing module 32 may decrement the transition counters to 0. Processing module 32 may cease delivery of recharge waveform 64 when the voltages $V_{C1}$ and $V_{C2}$ reach 0V in examples where the transition counters have a value of zero. A transition counter value of 0 may indicate to processing module 32 that upon a return of $V_{C1}$ and $V_{C2}$ to 0V, a charge balanced waveform has been delivered. Accordingly, processing module 32 may determine when to stop delivery of recharge waveform 64 based on when the voltages $V_{C1}$ and $V_{C2}$ reach 0V while the transition counters are at 0. Since $V_{C1}$ and $V_{C2}$ may not reach 0V at exactly the same time, processing module 32 may cease delivery of recharge waveform 64 when either of the voltages $V_{C1}$ and $V_{C2}$ reach 0V in some examples.

In some examples, charge may remain on one or more of coupling capacitors 52-1, 52-2. Such remaining charge may be indicative of a possible error in charge balance. Processing module 32 may control the delivery of stimulation such that the recharge waveform continues until most, or all, of the coupling capacitors are discharged. However, in some examples, charge may remain on one or more of the coupling capacitors when, at the end of a recharge waveform, there ceases to be a current path through the body for further discharge of the coupling capacitors. For example, there may cease to be a current path through the body when the only electrode(s) that remain unbalanced are either all anodes or all cathodes.

Figure 17:
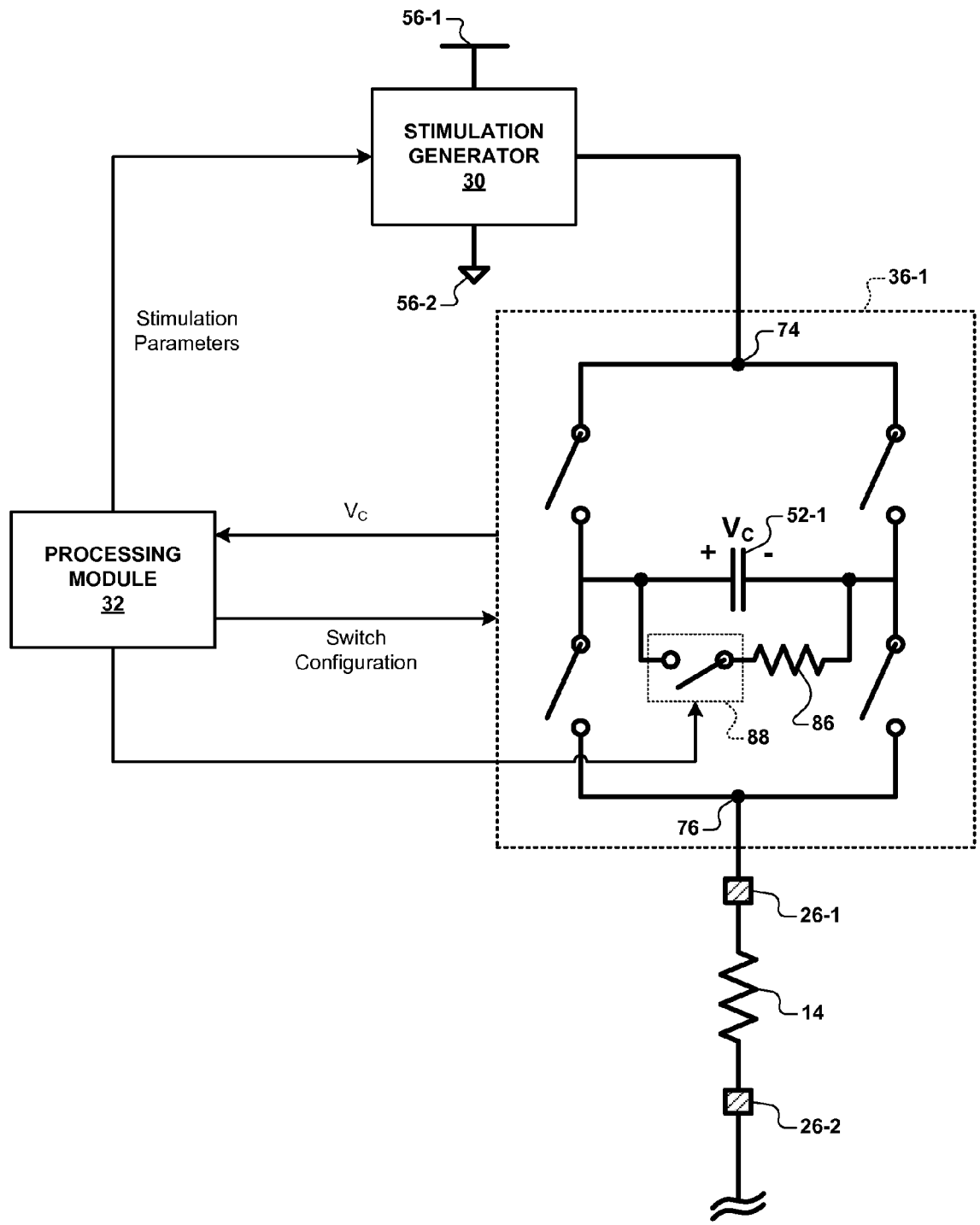
FIG. 17 illustrates an example coupling circuit including a resistor that discharges a coupling capacitor.

In examples where some charge remains on one or more of coupling capacitors 52-1, 52-2, the remaining charge may be discharged. In some examples, coupling circuits 36-1, 36-2 may include resistances through which remaining charge on coupling capacitors 52-1, 52-2 may be dissipated. For example, with respect to FIG. 17, coupling circuit 36-1 may have a resistor 86 that may be selectively connected between terminals of coupling capacitor 52-1. Resistor 86 may be selectively connected via a switch 88 controlled by processing module 32. When coupling capacitor 52-1 is connected to resistor 86, the remaining charge may dissipate from coupling capacitor 52-1.

In some examples, where charge remains on one or more of coupling capacitors 52-1, 52-2, the remaining charge may be retained until delivery of the next biphasic waveform. During the next biphasic waveform, processing module 32 may control the delivery of the biphasic waveform such that the one or more of coupling capacitors 52-1, 52-2 that included remaining charge after the prior biphasic waveform are discharged to 0V at the end of the recharge waveform. Subsequently, if another one or more of the coupling capacitors includes remaining charge after delivery of another biphasic waveform, processing module 32 may control the coupling circuits including those coupling capacitors that included remaining charge such that the coupling capacitors having the remaining charge are discharged at the end of the next biphasic waveform. In this manner, processing module 32 may control the coupling circuits to discharge coupling capacitors that include remaining charge during subsequent deliveries of biphasic waveforms. This may result in the delivery of more charge balanced waveforms over a period of time during which multiple biphasic waveforms are delivered.

In some examples, processing module 32 may control stimulation generator 30 to modify electrical stimulation delivered to a coupling capacitor including remaining charge in order to charge balance subsequent biphasic waveforms. For example, processing module 32 may increase or decrease the amount of stimulation provided via the coupling capacitor that included remaining charge in order to compensate for any imbalance. Processing module 32 may increase the recharge current for those coupling capacitors which do not complete recharge. This may cause the recharge for such capacitors to complete sooner while a recharge path still exists. In order that the recharge current magnitudes do not ratchet upwards over time, processing module 32 may decrease the recharge current magnitude for those electrodes which complete their recharge first among those electrodes engaged concurrently.

Although delivery of a single biphasic waveform (e.g., FIG. 14) is illustrated and described herein, IMD 16 according to the present disclosure may deliver other biphasic waveforms having different parameters. For example, IMD 16 may deliver biphasic waveforms having different pulse and recharge amplitudes, polarities, and/or durations. A change in pulse and recharge parameters may change the number of transitions during the pulse and/or recharge portions of the biphasic waveform.

Figure 15:
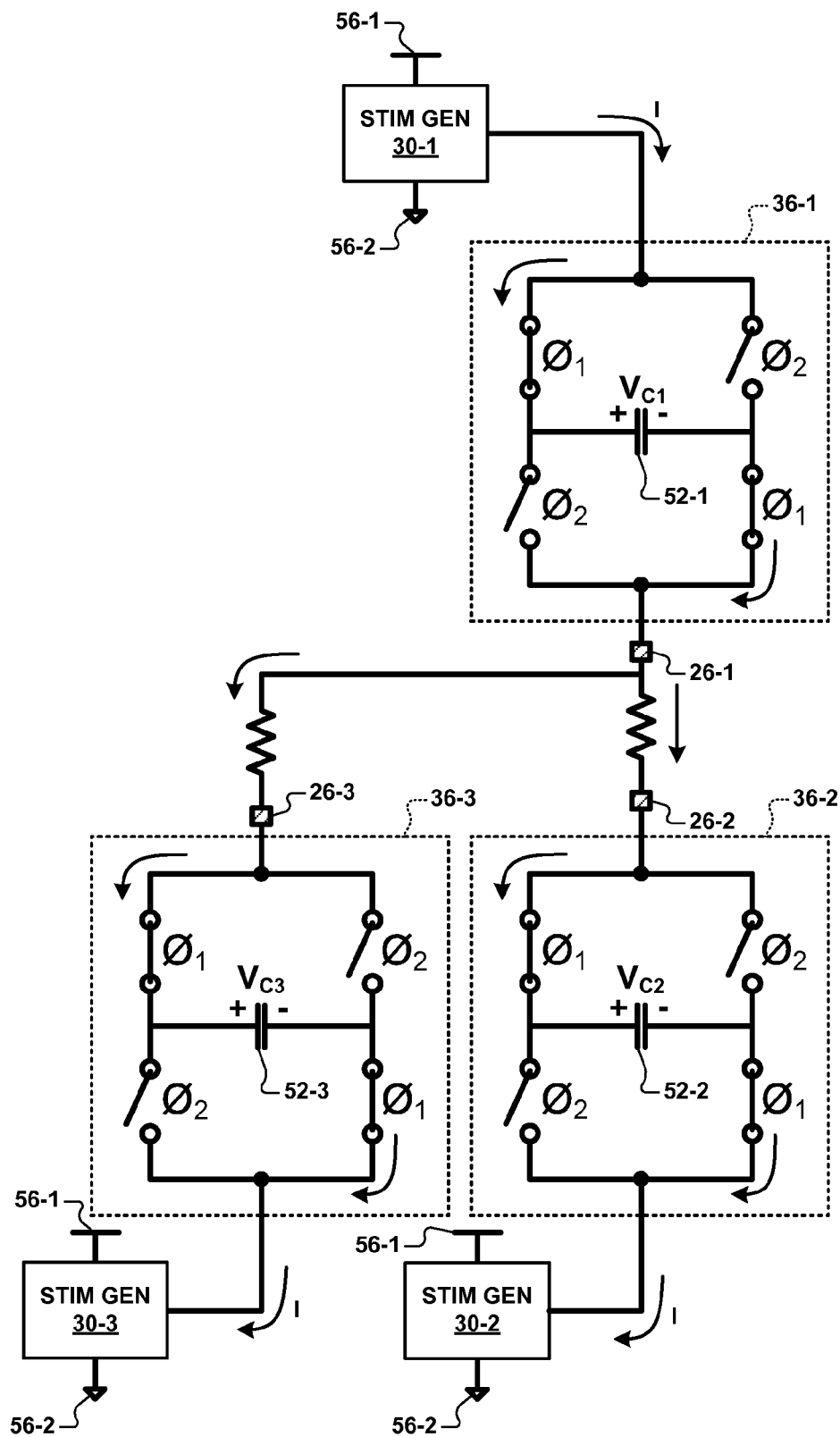
FIG. 15 shows an example system in which electrical stimulation is delivered between three electrodes.

Although delivery of electrical stimulation between two electrodes is illustrated in FIGS. 12A-13B, a coupling circuit of the present disclosure may be implemented in systems in which electrical stimulation is delivered between other numbers of electrodes. For example, FIG. 15 shows an example system in which electrical stimulation is delivered between three electrodes 26-1, 26-2, 26-3. Processing module 32 may control stimulation generators 30-1, 30-2, 30-3, which may be respective stimulation engines, and coupling circuits 36-1, 36-2, 36-3 in a similar manner as described above. For example, during delivery of pulse 62 and recharge waveform 64, processing module 32 may control stimulation generator 30-1 to deliver an amount of stimulation that is equal to, but opposite in direction to, the amount of stimulation delivered by stimulation generators 30-2, 30-3.

Coupling circuits 36-1, 36-2, 36-3 may include voltage detection modules (e.g., similar to voltage detection module 78) that monitor the voltages across coupling capacitors 52-1, 52-2, 52-3. Processing module 32 may control the coupling states of coupling circuits 36-1, 36-2, 36-3 based on the voltages $V_{C1}$, $V_{C2}$, and $V_{C3}$ across coupling capacitors 52-1, 52-2, 52-3 in order to maintain the voltages $V_{C1}$, $V_{C2}$, and $V_{C3}$ within threshold voltage ranges. Additionally, processing module 32 may maintain transition counters for each of coupling circuits 36-1, 36-2, 36-3 in order to track the amount of times each of coupling capacitors 52-1, 52-2, 52-3 have been charged/discharged.

Figure 16:
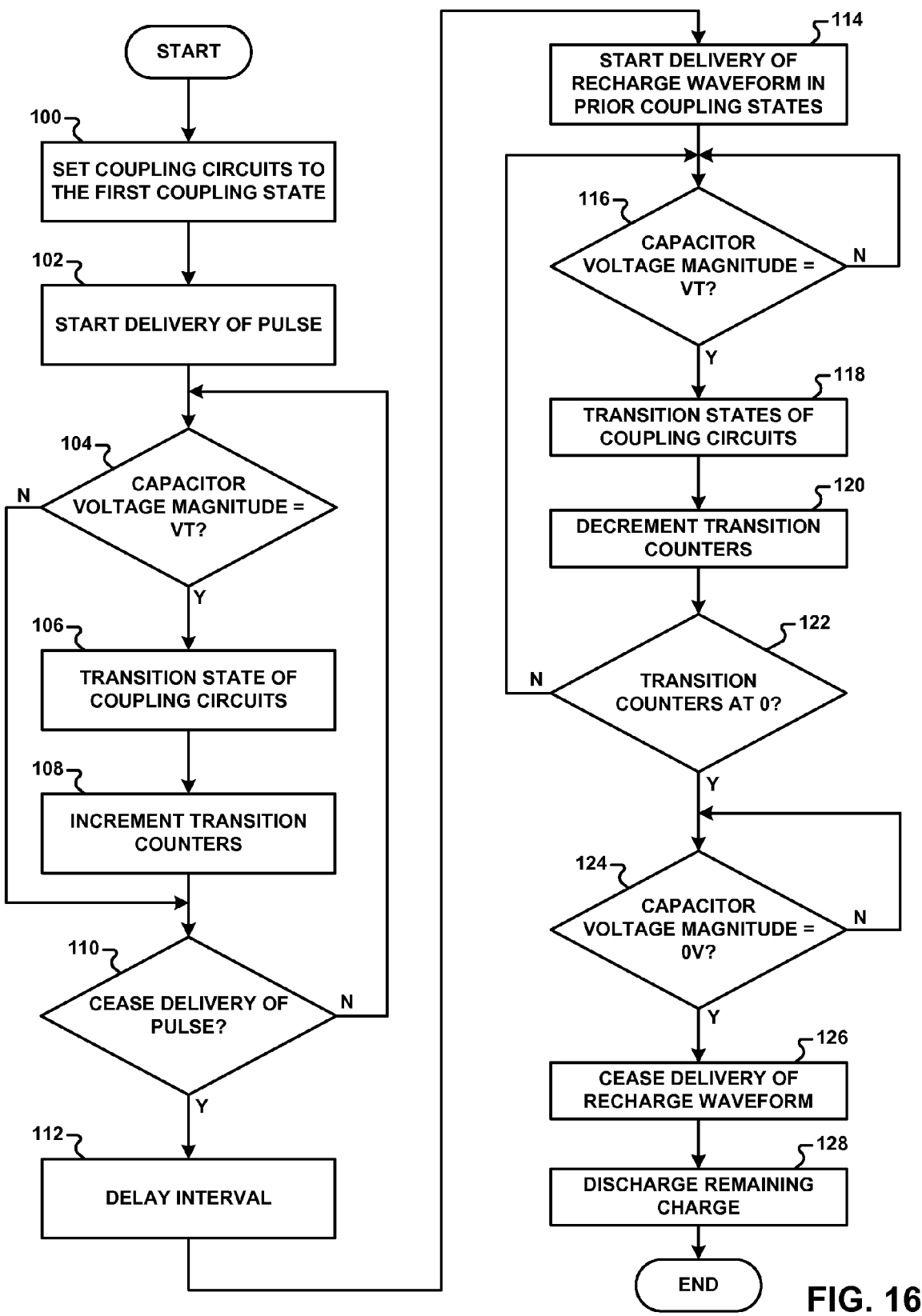
FIG. 16 shows an example method for delivering a charge-balanced biphasic waveform using a coupling circuit of the present disclosure.

FIG. 16 shows an example method for delivering charge balanced stimulation using a coupling circuit of the present disclosure. The method of FIG. 16 is described with respect to coupling circuits 36-1, 36-2 of FIGS. 12A-13B. Although processing module 32 may independently control the coupling states of coupling circuits 36-1, 36-2 because voltages $V_{C1}$ and $V_2$ may differ slightly during operation, it may be assumed that $V_{C1}$ and $V_{C2}$ are approximately equal for the purposes of describing the operation of IMD 16 according to the method of FIG. 16.

Initially, it may be assumed that coupling capacitors 52-1, 52-2 are discharged so that $V_{C1}$ and $V_{C2}$ are equal to 0V. Prior to delivery of pulse 62, processing module 32 may set coupling circuits 36-1, 36-2 to the first coupling state (100). Processing module 32 may then instruct stimulation generators 30-1, 30-2 to start delivery of pulse 62 (102). Processing module 32 may then determine when voltages $V_{C1}$ and $V_{C2}$ have reached the positive threshold voltage $V_T$ (104). It may be assumed that the capacitor voltages $V_{C1}$ and $V_{C2}$ may reach the voltage threshold $V_T$ at least once during delivery of stimulation. Accordingly, processing module 32 may initially determine that voltages $V_{C1}$ and $V_{C2}$ have reached the positive threshold voltage $V_T$.

In response to determining that voltages $V_{C1}$ and $V_{C2}$ have reached the positive threshold voltage $V_T$, processing module 32 transitions coupling circuits 36-1, 36-2 from the first coupling state to the second coupling state (106). Processing module 32 then increments the transition counters corresponding to coupling circuits 36-1, 36-2 upon transitioning coupling circuits 36-1, 36-2 to the second coupling state (108). Processing module 32 then determines whether to cease delivery of pulse 62 (110). If processing module 32 determines not to cease pulse 62, then the method continues at block (104) where processing module 32 determines whether the voltages $V_{C1}$ and $V_{C2}$ have reached the negative threshold voltage $-V_T$ during delivery of pulse (104). If processing module determines that voltages $V_{C1}$ and $V_{C2}$ have not reached $-V_T$, then processing module 32 may determine whether it is time to cease delivery of pulse 62 (110). If processing module 32 determines that it is not time to cease pulse 62, then the method may continue in blocks (104)-(108) in which transition counters for coupling circuits 36-1, 36-2 may be incremented in some examples, depending on how many times $V_{C1}$ and $V_{C2}$ reach the threshold voltages $-V_T$ and $V_T$.

If processing module 32 determines that it is time to cease pulse 62 in block (110), then processing module 32 may set coupling circuits 36-1, 36-2 to the open states for a delay interval 66 (112). Subsequent to delay interval 66, processing module 32 may set the coupling states of coupling circuits 36-1, 36-2 to the same coupling states as before delay interval 66. Processing module 32 may then control stimulation generators 30-1, 30-2 to start delivery of recharge waveform 64 (114).

Processing module 32 may then monitor voltages $V_{C1}$ and $V_{C2}$ to determine whether voltages $V_{C1}$ and $V_{C2}$ have reached a threshold magnitude $V_T$ (e.g., either $V_T$ or $-V_T$) (116). If processing module 32 determines that the voltages $V_{C1}$ and $V_{C2}$ have not reached a threshold magnitude $V_T$, then processing module 32 may continue monitoring voltages $V_{C1}$ and $V_{C2}$. In response to determining that voltages $V_{C1}$ and $V_{C2}$ have reached the threshold voltage magnitude $V_T$, processing module 32 may transition the coupling states of coupling circuits 36-1, 36-2 (118). Upon transitioning coupling states of coupling circuits 36-1, 36-2, processing module 32 may decrement the transition counters associated with coupling circuits 36-1, 36-2 (120).

Processing module 32 determines whether the transition counters are equal to zero (122). If the transition counters are not equal to zero, then processing module 32 may continue monitoring voltages $V_{C1}$ and $V_{C2}$ (116) until $V_{C1}$ and $V_{C2}$ reach a threshold magnitude $V_T$ and processing module 32 transitions coupling circuits 36-1, 36-2 another time (118). If the transition counter is zero in block (122), then processing module 32 may determine whether the voltages $V_{C1}$ and $V_{C2}$ have reached 0V (124). In response to determining that the voltages $V_{C1}$ and $V_{C2}$ have reached 0V, processing module 32 ceases delivery of recharge waveform 64 (126). Processing module 32 may then control the discharge of coupling capacitors that include any remaining charge (128).

Although a coupling circuit of the present disclosure may include a single coupling capacitor, it is contemplated that other coupling circuit elements may be included in the coupling circuit instead of a single coupling capacitor. In some examples, the coupling capacitor in a coupling circuit may be replaced by a network of capacitors connected in series and/or parallel with one another. In some examples, additional circuit components may be added along with the coupling capacitors. For example, resistive and/or inductive elements may be included in the coupling circuit along with coupling capacitors. Such additional circuit elements may provide different filtering characteristics than that provided by a single coupling capacitor. In other examples, active circuit components, such as amplifiers, may be included along with the coupling capacitor to form active filters, for example.

Although the voltages $V_{C1}$, $V_{C2}$, and $V_{C3}$ are described herein as ranging from a negative threshold voltage $-V_T$ to a positive threshold voltage $V_T$, the threshold voltages may be configured to different values. For example, if coupling capacitors 52-1, 52-2, 52-3 are polarized capacitors, the threshold voltages may both be set to the same polarity so that voltages across coupling capacitors 52-1, 52-2, 52-3 do not develop in a polarity that may adversely affect coupling capacitors 52-1, 52-2, 52-3. Accordingly, in some examples the voltage threshold range may be set from 0V to a positive threshold voltage $V_T$. In other examples, the voltage threshold range may be set from 0V to a negative threshold voltage $-V_T$.

In some examples, the threshold voltages (e.g., $\pm V_T$) may be values that are set throughout the life of IMD 16. In other examples, processing module 32 may adjust the threshold voltages. In some examples, a user may input a threshold voltage value into programmer 18, which may then be transferred to processing module 32. In other examples, processing module 32 may adjust the threshold voltage to provide power savings. Since a lower threshold voltage may increase the power efficiency of IMD 16, processing module 32 may decrease the threshold voltage to conserve power, e.g., during times when power source 40 is near depletion.

In some examples, processing module 32 may increase the threshold voltages such that the coupling circuit of the present disclosure may operate in a similar manner as the typical stimulation circuits of FIGS. 4A-4B. For example, processing module 32 may increase the threshold voltages to a voltage value that may not likely be attained during delivery of stimulation. In this example, processing module 32 may set the threshold voltage to a value near a maximum tolerable voltage for the coupling capacitor such that processing module 32 switches the state of the coupling circuit in order to prevent damage to the coupling capacitor. In still other examples, processing module 32 may ignore the voltage value across the coupling capacitors and maintain the coupling circuits in a single coupling state to operate the coupling circuit of the present disclosure as a typical stimulation circuit, e.g., of FIGS. 4A-4B.

In still other examples, processing module 32 may set the threshold voltage to a voltage value to avoid a transition that may result in a fault condition. For example, if a fault is detected in a coupling circuit during one of the first or second coupling states, processing module 32 may set the threshold voltage to avoid transitioning to the coupling state including the detected fault. In one example, if processing module 32 detects a fault in a switch of a coupling circuit during a first coupling state, then processing module 32 may set the threshold voltage for transitioning out of the second coupling state to a value that may not be reached while operating in the second coupling state. In this manner, processing module 32 may set the threshold voltage to a value that avoids a transition from the second coupling state back to the first coupling state which includes the detected fault. An example fault may include a "leaky" switch that may not be completely opened.

In some examples, processing module 32 may set the threshold voltage based on the number of transitions that occur during delivery of pulse 62 and/or recharge waveform 64. For example, if greater than a desirable number of transitions occur during delivery of pulse 62, then processing module 32 may increase the threshold voltage to reduce the number of total transitions during the delivery of a biphasic waveform. Similarly, to prevent switching during delivery of stimulation, processing module 32 may set the threshold voltage at a value that will not likely be reached during delivery of stimulation. In some examples, processing module 32 may determine the threshold voltage that may not likely be reached by iteratively increasing the threshold voltage until a transition does not occur during delivery of pulse 62.

In further examples, IMD 16 may include circuitry that is configured to deliver an electrical stimulation current of a first polarity to a patient via a capacitor 52-1, and switch the terminal of the capacitor 52-1 into which electrical stimulation current flows at least once during the delivery of the electrical stimulation current of the first polarity. In additional examples, the circuitry may be configured to switch the terminal of the capacitor 52-1 into which electrical stimulation current flows at least twice during the delivery of the electrical stimulation current of the first polarity. In some examples, the circuitry may correspond to one or more of stimulation generator 30, processing module 32, coupling circuits 36, and electrodes 26, 28 as described in this disclosure.

Delivering electrical stimulation current of a first polarity may correspond to delivering electrical stimulation in a first direction as described in this disclosure. In some examples, the electrical stimulation current of the first polarity may correspond to a pulse portion of a biphasic current waveform as described in this disclosure. In further examples, the electrical stimulation current of the first polarity may correspond to a recharge waveform of a biphasic current waveform as described in this disclosure.

Switching the terminal of capacitor 52-1 into which electrical stimulation current flows may correspond to switching the terminal of capacitor 52-1 into which electrical stimulation current flows between a first terminal of capacitor 52-1 and a second terminal of capacitor 52-1. For example, switching the terminal of capacitor 52-1 into which electrical stimulation current flows may include switching the terminal of capacitor 52-1 into which electrical stimulation current flows from a first terminal of capacitor 52-1 to a second terminal of capacitor 52-1, and switching the terminal of capacitor 52-1 into which electrical stimulation current flows from a second terminal of capacitor 52-1 to a first terminal of capacitor 52-1. The first and second terminals of capacitor 52-1 may be located on opposite sides of the dielectric in the capacitor 52-1.

When the terminal of capacitor 52-1 into which electrical stimulation current flows is switched to the first terminal of capacitor 52-1, then the stimulation pathway (e.g., coupling circuit 36-1) may be configured such that electrical stimulation current flows into the first terminal of capacitor 52-1 and out of the second terminal of capacitor 52-1. Similarly, when the terminal of capacitor 52-1 into which electrical stimulation current flows is switched to the second terminal of capacitor 52-1, then the stimulation pathway (e.g., coupling circuit 36-1) may be configured such that electrical stimulation current flows into the second terminal of capacitor 52-1 and out of the first terminal of capacitor 52-1.

Switching the terminal of capacitor 52-1 into which electrical stimulation current flows may correspond to switching the orientation of capacitor 52-1 as described in this disclosure. For example, if a first terminal of capacitor 52-1 is electrically coupled to stimulation generator 30 and a second terminal of capacitor 52-1 is electrically coupled to electrode 26-1, then IMD 16 may switch the orientation of capacitor 52-1 such that the first terminal of capacitor 52-1 is electrically coupled to electrode 26-1 and the second terminal of capacitor 52-1 is electrically coupled to stimulation generator 30. Similarly, if the first terminal of capacitor 52-1 is electrically coupled to electrode 26-1 and the second terminal of capacitor 52-1 is electrically coupled to stimulation generator 30, then IMD 16 may switch the orientation of capacitor 52-1 such that the first terminal of capacitor 52-1 is electrically coupled to stimulation generator 30 and the second terminal of capacitor 52-1 is electrically coupled to electrode 26-1. By switching the terminal of capacitor 52-1 that is electrically coupled to stimulation generator 30, IMD 16 may switch the terminal of capacitor 52-1 into which electrical stimulation current flows.

In some examples, switching the terminal of capacitor 52-1 into which electrical stimulation current flows may further correspond to switching a terminal of capacitor 52-1 out of which electrical stimulation current flows. In such examples, the circuitry may switch the terminal of the capacitor 52-1 into which electrical stimulation current flows and switch the terminal of the capacitor 52-1 out of which electrical stimulation current flows at least once during the delivery of the electrical stimulation current of the first polarity. The terminal of the capacitor 52-1 into which electrical stimulation current flows and the terminal of the capacitor 52-1 out of which electrical stimulation current flows may be opposite terminals of capacitor 52-1 (i.e., located on opposite sides of the dielectric in the capacitor 52-1).

In some examples, the circuitry included in IMD 16 may be further configured to switch the terminal of the capacitor into which the electrical stimulation current flows and/or switch the terminal of the capacitor out of which the electrical stimulation current flows based on a signal indicative of a magnitude of a voltage developed across the capacitor and/or based on a signal indicative of a charge stored in the capacitor. In some examples, the signal indicative of a magnitude of a voltage developed across the capacitor may be a signal generated by voltage detection module 78. For example, voltage detection module 78 may generate a signal indicative of whether a voltage across capacitor 52-1 is equal to, or greater than a threshold magnitude as described in this disclosure. In further examples, voltage detection module 78 may generate a signal that indicates the actual magnitude of the voltage across capacitor 52-1 without comparing the voltage to a threshold. In such examples, processing module 52 may perform one or more comparisons to determine when to switch capacitor 52-1.

In additional examples, a memristor may be electrically coupled in series between stimulation generator 30 and capacitor 52-1 or electrically coupled in series between capacitor 52-1 and electrode 26-1. In such examples, the resistance of the memristor may be indicative of the amount of charge that has traveled through the memristor over a given period of time, which may be further indicative of the amount of charge stored in capacitor 52-1, which may be further indicative of a magnitude of voltage across capacitor 52-1. Thus, the memristor may generate a signal (e.g., a resistance) indicative of a magnitude of voltage across capacitor 52-1 and/or a signal (e.g., a resistance) indicative of the charge stored in capacitor.

In further examples, the charge in the capacitor may be measured by integrating the current flowing through the capacitor. The integrator could be constructed using a small sensing resistor in series with the current path, and the voltage across the sensing resistor may be integrated over the time duration of current flowing through the capacitor. In such examples, the integrator may generate a signal indicative of the charge stored in the capacitor.

In more examples, the circuitry included in IMD 16 may be further configured to switch the terminal of the capacitor into which the electrical stimulation current flows based on a comparison of the signal indicative of the magnitude of the voltage developed across the capacitor to one or more thresholds. In some cases, the comparisons may correspond to the comparisons described with respect to decision blocks 104 and 116 in FIG. 16. In some examples, the one or more thresholds may correspond to $V_T$ and $-V_T$ as described in this disclosure. In further examples, the one or more thresholds may correspond to $V_T$ and 0V.

In some examples, the one or more thresholds may be selected based on the type of capacitor used for capacitor 52-1. For example, if capacitor 52-1 is a ceramic capacitor, then thresholds of $V_T$ and $-V_T$ may be selected. As another example, if capacitor 52-1 is a tantalum capacitor, then thresholds of $V_T$ and 0V may be selected. In further examples, the one or more thresholds may be selected based on a rated voltage of the capacitor.

In additional examples, the one or more thresholds may be selected based on a specified balance between power consumption and charge-balance accuracy. For example, choosing relatively high magnitude thresholds may be produce more accurate charge-balancing because there is less switching of the capacitors, while choosing relatively low magnitude thresholds may save power because the voltage needed to charge the capacitors does not need to be as high. A lower voltage requirement for charging the capacitor may save power in a battery-powered IMD because lower capacitor charging voltages may drain less power from the battery than higher capacitor charging voltages. In such examples, IMD 16 may be configured to use one or more thresholds for controlling the switching of capacitor 52-1 based on a specified balance between power consumption and charge-balance accuracy. In some examples, IMD 16 may be configured to receive user input (e.g., via a programmer) from a patient, programmer, and/or physician that specifies a balance between power consumption and charge-balance accuracy, and configure the one or more thresholds used by IMD 16 for controlling the switching of capacitor 52-1 based on the balance specified in the user input.

In some examples, in addition to the circuitry being configured to switch the terminal of the capacitor into which the electrical stimulation current flows at least once during delivery of the electrical stimulation current of the first polarity, the circuitry may be further configured to deliver an electrical stimulation current of a second polarity to the patient via the capacitor, and to switch the terminal of the capacitor into which the electrical stimulation current flows at least once during delivery of the electrical stimulation current of the second polarity. In additional examples, the circuitry may be configured to switch the terminal of the capacitor 52-1 into which electrical stimulation current flows at least twice during the delivery of the electrical stimulation current of the second polarity. The second polarity may be opposite the first polarity. In other words, the direction of the second polarity of the electrical stimulation current may be opposite the direction of the first polarity of the electrical stimulation current.

In further examples, the electrical stimulation current of the first polarity and the electrical stimulation of the second polarity may both be part of a biphasic electrical stimulation waveform. In such examples, the circuitry in IMD 16 may be further configured to cease to deliver electrical stimulation current of the second polarity in response to detecting that a number of times that the terminal of the capacitor into which electrical stimulation current flows has been switched during delivery of the electrical stimulation current of the second polarity is equal to a number of times that the terminal of the capacitor into which the electrical stimulation current flows has been switched during delivery of the electrical stimulation current of the first polarity and detecting that the capacitor is discharged. In some examples, IMD 16 may increment and decrement the transition counters described in this disclosure to detect when the number of capacitor switches for the second polarity is equal to the number of capacitor switches for the first polarity. In some examples, IMD 16 may use voltage detection module 78 to determine when the capacitor is discharged. Ensuring that the same number of switches occur for capacitor 52-1 in both the positive and negative phases of the biphasic waveform may ensure that charge-balancing will occur when capacitor 52-1 is discharged.

In additional examples, the circuitry in IMD 16 may deliver a biphasic electrical stimulation waveform to the patient during a stimulation cycle via a plurality of capacitors and a plurality of electrodes, each of the capacitors being electrically coupled to a respective one of the plurality of electrodes. The stimulation cycle may correspond to one or more periods of the biphasic electrical stimulation waveform. During the stimulation cycle, each electrode may deliver an electrical stimulation current in a first direction, and subsequently deliver an electrical stimulation in a second direction until charge-balance has been achieved for the respective electrode. Once charge-balance has been achieved, the electrode may cease delivery of electrical stimulation until the next stimulation cycle. Achieving charge balance may be performed using any of the techniques described in this disclosure including the technique illustrated in FIG. 16.

Because each of the electrodes is charge-balanced independent of the others, it is possible that not all electrodes will achieve charge balance at the same time. In some cases, all electrodes delivering electrical stimulation of a first polarity may achieve charge balance during a stimulation cycle prior to one or more of the electrodes delivering electrical stimulation of a second polarity. In such cases, the remaining electrodes may not have an electrical pathway to discharge. In some examples, IMD 16 may identify such electrodes, and adjust the recharge current magnitude for such electrodes during subsequent stimulation cycles to allow the electrodes to discharge faster and avoid a situation where the electrodes are not able to fully discharge.

For example, for each of the plurality electrodes, the circuitry in IMD 16 may be configured to cease delivering electrical stimulation current via the respective electrode during the stimulation cycle in response to detecting that a number of times that a terminal of a respective one of the capacitors into which electrical stimulation current flows has been switched during delivery of a first polarity of the biphasic electrical stimulation waveform is equal to a number of times that a terminal of the respective one of the capacitors into which the electrical stimulation current flows has been switched during delivery of a second polarity of the biphasic electrical stimulation waveform and that the respective one of the capacitors is discharged. The circuitry may be further configured to detect if all electrodes that have not ceased delivery of electrical stimulation current during the stimulation cycle are currently delivering electrical stimulation current of the same polarity, and adjust a magnitude of a recharge waveform for one or more of the electrodes to be delivered during subsequent biphasic electrical stimulation waveforms in response to detecting that all electrodes that have not ceased delivery of electrical stimulation current during the stimulation cycle are currently delivering electrical stimulation current of the same polarity.

The techniques described in this disclosure, including those attributed to IMD 16, programmer 18, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A device for delivering electrical stimulation to a patient, the device comprising;
    a capacitor; and
    circuitry configured to:
        deliver an electrical stimulation current of a first polarity to the patient via the capacitor; and
        switch a terminal of the capacitor into which the electrical stimulation current flows at least twice during delivery of the electrical stimulation current of the first polarity.

2. The device of claim 1, wherein the circuitry is further configured to switch the terminal of the capacitor into which the electrical stimulation current flows based on at least one of a signal indicative of a magnitude of a voltage developed across the capacitor and a signal indicative of a charge stored in the capacitor.

3. The device of claim 2, wherein the circuitry is further configured to switch the terminal of the capacitor into which the electrical stimulation current flows based on a comparison of the at least one of the signal indicative of the magnitude of the voltage developed across the capacitor and the signal indicative of the charge stored in the capacitor to one or more thresholds.

4. The device of claim 3, wherein the one or more thresholds are selected based on at least one of a type of capacitor and a rated voltage of the capacitor.

5. The device of claim 3, wherein the one or more thresholds are selected based on a specified balance between power consumption and charge-balance accuracy.

6. The device of claim 2, wherein the device comprises a voltage detection module that is configured to measure a voltage across the terminals of the capacitor, and generate the signal indicative of the magnitude of the voltage developed across the capacitor.

7. The device of claim 1, wherein the circuitry is further configured to:
    deliver an electrical stimulation current of a second polarity to the patient via the capacitor; and
    switch the terminal of the capacitor into which the electrical stimulation current flows at least once during delivery of the electrical stimulation current of the second polarity.

8. The device of claim 7, wherein the electrical stimulation current of the first polarity and the electrical stimulation current of the second polarity are both part of a biphasic electrical stimulation waveform, and wherein the circuitry is further configured to:
    cease delivering electrical stimulation current of the second polarity in response to detecting that a number of times that the terminal of the capacitor into which electrical stimulation current flows has been switched during delivery of the electrical stimulation current of the second polarity is equal to a number of times that the terminal of the capacitor into which the electrical stimulation current flows has been switched during delivery of the electrical stimulation current of the first polarity and detecting that the capacitor is discharged.

9. The device of claim 1, wherein the circuitry is further configured to:
    deliver a biphasic electrical stimulation waveform to the patient during a stimulation cycle via a plurality of capacitors and a plurality of electrodes, each of the capacitors being electrically coupled to a respective one of the plurality of electrodes;
    for each of the plurality electrodes, cease delivering electrical stimulation current via the respective electrode during the stimulation cycle in response to detecting that a number of times that a terminal of a respective one of the capacitors into which electrical stimulation current flows has been switched during delivery of a first polarity of the biphasic electrical stimulation waveform is equal to a number of times that a terminal of the respective one of the capacitors into which the electrical stimulation current flows has been switched during delivery of a second polarity of the biphasic electrical stimulation waveform and that the respective one of the capacitors is discharged;
    detect if all electrodes that have not ceased delivery of electrical stimulation current during the stimulation cycle are currently delivering electrical stimulation current of the same polarity; and
    adjust a magnitude of a recharge waveform for one or more of the electrodes to be delivered during subsequent biphasic electrical stimulation waveforms in response to detecting that all electrodes that have not ceased delivery of electrical stimulation current during the stimulation cycle are currently delivering electrical stimulation current of the same polarity.

10. The device of claim 1, wherein the circuitry comprises:
    an electrical stimulation generator configured to generate the electrical stimulation current;
    a coupling circuit comprising a first node connected to the electrical stimulation generator, a second node configured to deliver the electrical stimulation current to the patient, and the capacitor, the coupling circuit being configured to, during delivery of the electrical stimulation current of the first polarity:

operate in a first state to couple the capacitor between the first and second nodes in a first orientation; and operate in a second state to couple the capacitor between the first and second nodes in a second orientation that is opposite to the first orientation; and a processing module configured to set the state of the coupling circuit to one of the first and second states.

11. The device of claim 10, wherein the coupling circuit comprises a plurality of switches, wherein the switches are configured to connect the capacitor between the first and second nodes in the first orientation, wherein the switches are configured to connect the capacitor between the first and second nodes in the second orientation, and wherein the processing module is configured to set the states of the switches to set the coupling circuit to one of the first and second states.

12. The device of claim 10, wherein the processing module is configured to set the state of the coupling circuit to maintain the voltage across the capacitor within a threshold voltage range.

13. The device of claim 12, wherein the threshold voltage range is defined by a first threshold voltage and a second threshold voltage, wherein the processing module is configured to change the state of the coupling circuit from the first state to the second state when the voltage across the capacitor reaches the first threshold voltage, and wherein the processing module is configured to change the state of the coupling circuit from the second state to the first state when the voltage across the capacitor reaches the second threshold voltage.

14. The device of claim 10, wherein the electrical stimulation generator is configured to deliver current to the coupling circuit that charges the capacitor to a first voltage polarity when the capacitor is in the first orientation and charges the capacitor to a second voltage polarity that is opposite to the first voltage polarity when the capacitor is in the second orientation.

15. The device of claim 14, wherein the processing module is configured to transition the coupling circuit from the first state to the second state when the capacitor is in the first orientation and the voltage across the capacitor is equal to a positive threshold voltage, and wherein the processing module is configured to transition the coupling circuit from the second state to the first state when the capacitor is in the second orientation and the voltage across the capacitor is equal to a negative threshold voltage.

16. The device of claim 10, wherein the electrical stimulation generator is configured to generate a biphasic electrical stimulation waveform comprising a pulse portion having a first polarity and a subsequent recharge portion having a second polarity that is opposite to the first polarity, wherein the second node is configured to deliver the biphasic electrical stimulation waveform to the patient, and wherein the processing module is configured to transition the coupling circuit between the first and second states during the pulse portion to maintain a voltage across the capacitor within a threshold voltage range.

17. The device of claim 16, wherein the processing module is further configured to:
count a number of transitions during the pulse portion;
transition the coupling circuit between the first and second states during the recharge portion to maintain the voltage across the capacitor within the threshold voltage range;
decrement the number of transitions counted during the pulse portion for each transition during the recharge portion; and
determine that the biphasic electrical stimulation waveform is charge-balanced after the number of transitions has been decremented to zero.

18. The device of claim 10, further comprising a housing configured for implantation in the patient, wherein the housing encloses the electrical stimulation generator, the coupling circuit, and the processing module.

19. The device of claim 10, wherein the second node is configured to electrically connect to an electrode configured for implantation in the patient.

20. A device for delivering electrical stimulation to a patient, the device comprising:
a capacitor;
means for delivering an electrical stimulation current of a first polarity to the patient via the capacitor; and
means for switching a terminal of the capacitor into which the electrical stimulation current flows at least twice during delivery of the electrical stimulation current of the first polarity.

21. The device of claim 20, further comprising:
means for generating electrical stimulation; and
means for capacitively coupling the generated electrical stimulation to the patient using the capacitor, wherein the means for capacitively coupling comprises:
means for orienting the capacitor in a first orientation during delivery of the electrical stimulation of the first polarity to the patient; and
means for orienting the capacitor in a second orientation during delivery of the electrical stimulation of the first polarity to the patient, wherein the second orientation is opposite to the first orientation; and
means for setting the orientation of the capacitor to one of the first and second orientations during delivery of the electrical stimulation of the first polarity.

22. The device of claim 21, further comprising means for setting the orientation of the capacitor based on a magnitude of a voltage developed across the capacitor.

23. A method for delivering electrical stimulation to a patient, the method comprising:
delivering, via a capacitor of a device, an electrical stimulation current of a first polarity to the patient; and
switching a terminal of the capacitor into which the electrical stimulation current flows at least twice during delivery of the electrical stimulation current of the first polarity.

24. The method of claim 23, further comprising
generating electrical stimulation;
capacitively coupling the generated electrical stimulation to the patient using the capacitor, wherein capacitively coupling the generated electrical stimulation comprises:
orienting the capacitor in a first orientation during delivery of the electrical stimulation of the first polarity to the patient; and
orienting the capacitor in a second orientation during delivery of the generated electrical stimulation of the first polarity to the patient, wherein the second orientation is opposite to the first orientation; and
setting the orientation of the capacitor to one of the first and second orientations during delivery of the electrical stimulation of the first polarity.

25. The method of claim 24, further comprising setting the orientation of the capacitor based on a magnitude of a voltage developed across the capacitor.

* * * * *